US 7,091,348 B2
Aug. 15, 2006

(12) United States Patent
O'Neill et al.

(10) Patent No.: US 7,091,348 B2
(45) Date of Patent: Aug. 15, 2006

(54) FLUORESCENT DYES, ENERGY TRANSFER COUPLES AND METHODS

(75) Inventors: Roger O'Neill, San Carlos, CA (US); Peter V. Fisher, Hayward, CA (US)

(73) Assignee: Guava Technologies, Inc., Hayward, CA (US)

(*) Notice: Subject to any disclaimer, the term of this patent is extended or adjusted under 35 U.S.C. 154(b) by 29 days.

(21) Appl. No.: 10/612,297

(22) Filed: Jul. 1, 2003

(65) Prior Publication Data

US 2004/0073014 A1    Apr. 15, 2004

Related U.S. Application Data

(60) Provisional application No. 60/422,621, filed on Oct. 30, 2002, provisional application No. 60/393,338, filed on Jul. 1, 2002.

(51) Int. Cl.
*C07D 209/06* (2006.01)
*C07D 215/04* (2006.01)
*C07D 487/02* (2006.01)

(52) U.S. Cl. .................. 544/280; 546/152; 548/455
(58) Field of Classification Search ............... 544/280; 546/152; 548/455
See application file for complete search history.

(56) References Cited

U.S. PATENT DOCUMENTS

| | | | |
|---|---|---|---|
| 5,106,990 A | 4/1992 | Ohno et al. |
| 5,268,486 A | 12/1993 | Waggoner et al. |
| 5,453,505 A | 9/1995 | Lee et al. |
| 5,486,616 A | 1/1996 | Waggoner et al. |
| 5,539,082 A | 7/1996 | Nielsen et al. |
| 5,569,766 A | 10/1996 | Waggoner et al. |
| 5,571,388 A | 11/1996 | Patonay et al. |
| 5,616,502 A | 4/1997 | Haugland et al. |
| 5,648,270 A | 7/1997 | Kuhn et al. |
| 5,650,334 A | 7/1997 | Zuk et al. |
| 5,679,516 A | 10/1997 | Okamoto et al. |
| 5,688,966 A | 11/1997 | Bobrow et al. |
| 5,710,628 A | 1/1998 | Waterhouse et al. |
| 5,714,386 A | 2/1998 | Roederer |
| 5,719,027 A | 2/1998 | Miyazaki et al. |
| 5,723,218 A | 3/1998 | Haugland et al. |
| 5,755,943 A | 5/1998 | Middendorf et al. |
| 5,767,287 A | 6/1998 | Bobrow et al. |
| 5,783,673 A | 7/1998 | Gupta |
| 5,800,995 A | 9/1998 | Patoney et al. |
| 5,804,448 A | 9/1998 | Wang et al. |
| 5,808,044 A | 9/1998 | Brush et al. |
| 5,821,066 A | 10/1998 | Pyle et al. |
| 5,852,191 A | 12/1998 | Karandikar et al. |
| 5,863,403 A | 1/1999 | Middendorf et al. |
| 5,877,310 A | 3/1999 | Reddington et al. |
| 5,935,522 A | 8/1999 | Swerdlow et al. |
| 5,981,747 A | 11/1999 | Mujumdar et al. |
| 5,986,086 A | 11/1999 | Brush et al. |
| 6,004,446 A | 12/1999 | Middendorf et al. |
| 6,004,536 A | 12/1999 | Leung et al. |
| 6,005,663 A | 12/1999 | Waterhouse et al. |
| 6,008,373 A | 12/1999 | Waggoner et al. |
| 6,013,802 A | 1/2000 | Hoyland et al. |
| 6,014,213 A | 1/2000 | Waterhouse et al. |
| 6,027,709 A | 2/2000 | Little et al. |
| 6,043,025 A | 3/2000 | Minden et al. |
| 6,086,737 A | 7/2000 | Patonay et al. |
| 6,110,630 A | 8/2000 | Reddy et al. |
| 6,114,350 A | 9/2000 | Randall et al. |
| 6,120,987 A | 9/2000 | Aspe |
| 6,127,134 A | 10/2000 | Minden et al. |
| 6,130,094 A | 10/2000 | Waggoner et al. |
| 6,130,101 A | 10/2000 | Mao et al. |
| 6,136,612 A | 10/2000 | Della Ciana et al. |
| 6,140,494 A | 10/2000 | Hamilton et al. |
| 6,143,151 A | 11/2000 | Middendorf |
| 6,146,837 A | 11/2000 | van de Winkel |
| 6,197,956 B1 | 3/2001 | Randall et al. |
| 6,200,766 B1 | 3/2001 | Davis |
| 6,201,112 B1 | 3/2001 | Ach |
| 6,207,421 B1 | 3/2001 | Middendorf et al. |
| 6,207,464 B1 | 3/2001 | Karandikar et al. |
| 6,224,644 B1 | 5/2001 | Randall et al. |
| 6,248,904 B1 | 6/2001 | Zhang et al. |
| 6,294,667 B1 | 9/2001 | Jackson et al. |
| 6,299,839 B1 | 10/2001 | Karunaratne et al. |
| 6,329,144 B1 | 12/2001 | Kubista et al. |
| 6,342,611 B1 | 1/2002 | Weber et al. |
| 6,376,202 B1 | 4/2002 | Davis |
| 6,383,749 B1 | 5/2002 | Bochkariov et al. |
| 6,397,150 B1 | 5/2002 | Izmailov |
| 6,399,392 B1 | 6/2002 | Haugland et al. |
| 6,403,378 B1 | 6/2002 | Phi-Wilson et al. |
| 6,403,807 B1 | 6/2002 | Singh et al. |
| 6,423,505 B1 | 7/2002 | Davis |
| 6,426,190 B1 | 7/2002 | Minden et al. |

(Continued)

OTHER PUBLICATIONS

Landsdorp, et al.; "Single Laser three Color Immunofluorescence Staining Procedures Based on Energy Transfer Between Phycoerythrin and Cynanine 5"; Cytometry 12:723-730 (1991).

(Continued)

*Primary Examiner*—Taofiq Solola
(74) *Attorney, Agent, or Firm*—David W. Maher

(57) ABSTRACT

Fluorescent dyes, fluorescence energy transfer dye couples, multi-color dye sets, can be employed in art-recognized assays and certain novel methods, such as in proximity assays.

17 Claims, No Drawings

U.S. PATENT DOCUMENTS

| | | |
|---|---|---|
| 6,437,141 B1 | 8/2002 | Randell et al. |
| 6,479,303 B1 | 11/2002 | Waggoner et al. |
| 6,540,977 B1 | 4/2003 | van de Winkel |
| 6,545,164 B1 | 4/2003 | Waggoner et al. |
| 6,673,943 B1 | 1/2004 | Waggoner et al. |
| 6,706,879 B1 | 3/2004 | Anderson et al. |
| 6,716,994 B1 | 4/2004 | Menchen et al. |
| 6,723,509 B1 | 4/2004 | Ach |
| 6,734,310 B1 | 5/2004 | Reiner et al. |
| 6,747,159 B1 | 6/2004 | Caputo et al. |
| 6,821,708 B1 | 11/2004 | Liao et al. |
| 6,838,289 B1 | 1/2005 | Bell et al. |
| 2003/0068577 A1 | 4/2003 | Liao et al. |

OTHER PUBLICATIONS

Mujumdar, et al.; "Cyanine Dye Labeling Reagents: Sulfoindocyanine Succinimidyl Esters"; Bioconjugate Chem., vol. 4, No. 2, 1993; American Chemical Society.

FLUORESCENT DYES, ENERGY TRANSFER COUPLES AND METHODS

CROSS-REFERENCE TO RELATED APPLICATONS

This application claims the benefit of now abandoned provisional U.S. Applications Ser. No. 60/393,338, filed Jul. 1, 2002 and Ser. No. 60/422,621, filed Oct. 30, 2002, both incorporated herein by reference.

FIELD OF THE INVENTION

This invention relates to fluorescent dyes, fluorescence energy transfer, particularly to fluorescence energy transfer dye sets, donor dyes, acceptor/reporter dyes, linkers, combinations and methods of their use, e.g., in flow cytometry, DNA sequencing, protein arrays, DNA arrays, markers in microscopy. The compounds of the invention useful individually and particularly for multiplexing.

BACKGROUND OF THE INVENTION

The non-radioactive detection of biological analytes utilizing fluorescent labels is an important technology in modern analytical biotechnology. By eliminating the need for radioactive labels, safety is enhanced and the environmental impact of reagent disposal is greatly reduced. Examples of methods utilizing such fluorescent detection methods include DNA sequencing, oligonucleotide probe methods, polymerase-chain-reaction product detection, immunoassays, and the like.

One example of analytical equipment employing fluorescent dyes is flow cytometry, a method for detecting, classifying, and characterizing various analytes including biological cells and other particles such as viruses or molecules that exhibit specific characteristics. In a flow cytometer, a flowing liquid stream containing analytes in a liquid medium is directed to an irradiation region. A radiation source, usually a laser, irradiates the analytes, and optical and electronic detection equipment and processors are used to measure spectral properties of the sample, including light absorption, scattering, fluorescence, or phosphorescence to detect the presence of the analytes.

The use of simple fluorescent markers typically entails a purification step to separate bound and unbound fluorescent markers, in order to obtain precise measurements without background interference from the (unbound or bound) group not being measured. Such purification steps add undesired time and expense to what should be a rapid automated process.

In many important applications the independent detection of multiple spatially overlapping analytes in a mixture is required, e.g., single-tube multiplex DNA probe assays, immuno assays, multicolor DNA sequencing methods, and the like. In the case of multi-loci DNA probe assays, by employing spectrally distinguishable fluorescent labels, the number of reaction tubes can be reduced thereby simplifying experimental protocols and facilitating the manufacturing of application-specific kits. In the case of automated DNA sequencing, multicolor fluorescent labeling allows for the analysis of multiple bases in a single lane thereby increasing throughput over single-color methods and reducing uncertainties associated with inter-lane electrophoretic mobility variations.

Multi-color fluorescent detection imposes five severe constraints on the selection of dye labels, particularly for applications requiring a single excitation light source, an electrophoretic separation, and/or treatment with enzymes, e.g., automated fluorescence-based DNA sequencing. First, it is difficult to find a set of dyes whose emission spectra are spectrally resolved, since the typical emission band half-width for organic fluorescent dyes is about 40–80 nanometers (nm) and the width of available spectrum is limited by the excitation light source. Second, even if dyes with non-overlapping emission spectra are found, the set may still not be suitable if the respective fluorescent efficiencies are too low. Third, when several fluorescent dyes are used concurrently, simultaneous excitation becomes difficult because the absorption bands of the dyes are widely separated. Fourth, the charge, molecular size, and conformation of the dyes must not adversely affect the electrophoretic mobilities of the analyte. Fifth, the fluorescent dyes must be compatible with the chemistry used to create or manipulate the analyte, e.g., DNA synthesis solvents and reagents, buffers, polymerase enzymes, ligase enzymes, and the like. (See, e.g., U.S. Pat. No. 6,008,379.)

One of the limitations of such presently available technologies arises from the available pool of restriction enzymes. These produce a correspondingly limited pool of restriction sites and, therefore, fragments to be detected. Another limitation pertains to the nature of information that is discoverable, i.e., whether the identified target is present, and its relative concentration. It is not, however, readily possible to determine the relative proximity of target sites to each other under fixed or changing environmental conditions.

Fluorescence energy transfer ("FET") and fluorescence resonance energy transfer ("FRET") are distance-dependent excited state interactions in which emission of one fluorophore is coupled to the excitation of another. These processes employ two fluorescent dye molecules, one, a donor (D1), having relatively shorter wavelength excitation and emission spectra, and the other dye, an acceptor/reporter (D2), having longer wavelength excitation and emission spectra. Excitation of D1 by a light source of appropriate wavelength ultimately results in emission by D2 at its characteristic wavelength. D1 and D2 must be sufficiently proximate (within about 100 Å) to facilitate energy transfer; this can be accomplished in a number of manners (e.g., via linking to solid supports) or, in the special case of direct fluorescence energy transfer, D1 and D2 can be physically linked together (e.g., through a chain of covalently linked atoms). In general, when D1 is excited (at a shorter, higher energy wavelength) it re-emits a photon at a longer wavelength (within D1's emission spectrum), and this re-emitted photon is in turn absorbed by D2 to produce an excited state. As D2 returns to its ground state, it emits a photon of light at a wavelength characteristic of its spectrum. In radiation-less energy transfer, the reporter dipole interacts or resonates with the donor dipole where the energy level difference between the fluorophores corresponds to the quantum of excitation energy. In this process, the quantum, or exciton, is transferred, which raises the electron in the reporter to a higher energy state as the photo-excited electron in the donor returns to ground state. D1 transmits its excitation energy directly to D2 through the chain of linking atoms, without D1 ever releasing a photon. After D2 absorbs this energy it returns to its ground state while emitting a photon. Conditions include that the fluorescent emission spectrum of the energy donor overlap the absorption spectrum of the energy reporter, and that the donor and reporter transition dipole orientations must be approximately parallel. Energy transfer may be detected from an increase in reporter emission or a decrease in donor emission. In either case (direct or indirect) the result of such energy transfer is that D2 can be induced to emit a photon where the initial excitation light put into the system is of a wavelength that would not normally excite D2.

Notwithstanding the available fluorescent dyes and their application in various analytical methods including simple fluorescence, FET and FRET, it has remained desired to provide new and improved fluorescent dyes, FET and FRET dye couples, multiple-color energy transfer sets and methods of their use, particularly where no purification to remove excess fluorescent marker is required to achieve a satisfactory detection signal.

SUMMARY OF THE INVENTION

The present invention provides certain fluorescent dyes, dye linkers and dye couples, for example as represented by Formula I:

-L1-D1-FETL-D2-L2     (Formula I)

where:
L1 is a link for attachment to a probe or target, for attachment to a solid support, or is absent;
L2 is a link for attachment to a probe or target, for attachment to a solid support, or is absent; and
FETL is a fluorescence energy transfer linker comprising a symmetric, rigid or sterically hindered, divalent moiety joined to D1 and D2 via an amine, carbonyl, activated carboxylic acid ester, disulfide, thiol or thiol ester;
D1 is a donor dye represented by the formula:

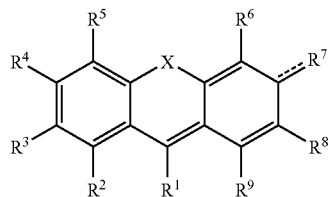

D1 where:
X is O or C(R*R**), where R* and R** are independently lower alkyl or —CH$_2$-Z;
R$^1$ is H, CF$_3$, perfluoropropyl, lower alkyl acid, substituted aryl (preferably 5–6 membered mono or 10–12 membered fused, esp. o-benzoic acid), substituted heteroaryl (5–6 membered mono or 10–12 membered fused) or Z;
R$^2$ is H, halo, SO$_3^-$, or is taken together with R$^3$ to form an optionally substituted fused ring having 5 to 7 atoms (preferably a 6-membered aryl ring);
R$^3$ is halo (preferably chloro), Z, or is taken together with R$^2$ and/or R$^4$ to form an optionally substituted fused ring having 5 to 7 atoms (preferably a 6-membered ring);
R$^4$ is =O or OH, —N(R$^{4'}$R$^{4''}$) or =N$^+$(R$^{4'}$R$^{4''}$), or is taken together with R$^3$ and/or R$^5$ to form an optionally substituted fused ring having 5 to 7 atoms (preferably a 6-membered ring),
where R$^{4'}$ is H, lower alkyl or L1, and
R$^{4''}$ is H, lower alkyl or CH$_2$-Z;
R$^5$ is H, halo, Z, or is taken together with R$^4$ to form an optionally substituted fused ring having 5 to 7 atoms (preferably a 6-membered ring);
R$^6$ is H, halo, Z, or is taken together with R$^7$ to form an optionally substituted fused ring having 5 to 7 atoms (preferably a 6-membered ring);
R$^7$ is =O or OH, —N(R$^{7'}$R$^{7''}$) or =N$^+$(R$^{7'}$R$^{7''}$), or is taken together with R$^6$ and/or R$^8$ to form an optionally substituted fused ring having 5 to 7 atoms (preferably a 6-membered ring),
where R$^{7'}$ is H, lower alkyl or L1, and
R$^{7''}$ is H, lower alkyl or CH$_2$-Z;
R$^8$ is halo (preferably chloro), Z, or is taken together with R$^7$ and/or R$^9$ to form an optionally substituted fused ring having 5 to 7 atoms (preferably a 6-membered ring);
R$^9$ is H, halo, SO$_3^-$, or is taken together with R$^8$ to form an optionally substituted fused ring having 5 to 7 atoms (preferably a 6-membered aryl ring); and
Z is a group of the formula: -Z*-Z$^1$-(L1, L2 or FETL), where:
Z* is methylene, methoxy, ethoxy, aminomethyl, aminoethyl, aminopropynyl, aminobutynyl, carboxyethenyl, carboxyethynyl, optionally substituted aryl or optionally substituted heteroaryl;
Z$^1$ is —C(O)—, —N(Z$^2$)-, —CH$_2$—O—, —CH$_2$—C(O)—, —CH$_2$—N(Z$^2$)—, —CH$_2$—S-, —CH$_2$—S(O)—, —CH$_2$—S(O$_2$)— or is absent; and
Z$^2$ is H, C$_1$ to C$_8$ optionally substituted lower alkyl, or optionally substituted aryl (substituents preferably SO$_3^-$, COOH, NH$_2$, CH$_2$NH$_2$, SH, SCH$_3$); and D2 is an acceptor/reporter dye represented by formula D1 or by a formula of the group:

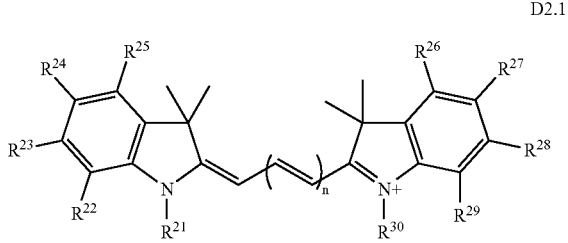

D2.1

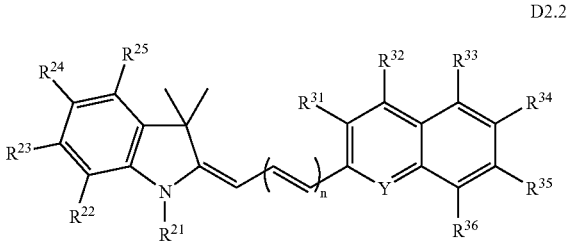

D2.2

-continued

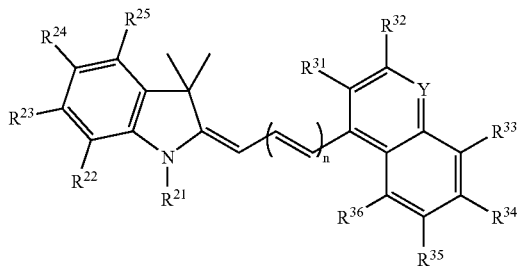
D2.3

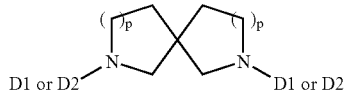
FETL3 where:
p is independently 0, 1, 2 or 3; and

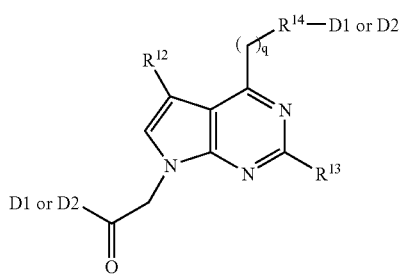
FETL4 where:
at least one of $R^{21}$ to $R^{36}$ is joined to FETL,
n is zero, 1, 2 or 3;
$R^{21}$ and $R^{30}$ are independently —CH$_2$-Z, activated lower alkyl, or optionally substituted aralkyl;
$R^{22}$ to $R^{29}$ are independently H, SO$_3^-$, or optionally substituted alkyl, or $R^{22}$ and $R^{23}$, $R^{23}$ and $R^{24}$ $R^{24}$ and $R^{25}$, $R^{26}$ and $R^{27}$, $R^{27}$ and $R^{28}$, and/or $R^{28}$ and $R^{29}$ taken together form an optionally substituted fused ring having 6 atoms (preferably sulfonated aryl ring); and
$R^{31}$ and $R^{32}$ are independently H, optionally substituted alkyl, aryl, or taken together form an optionally substituted fused ring having 6 atoms (preferably sulfonated carbocyclic or heterocyclic ring);
$R^{33}$ to $R^{36}$ are independently H, SO$_3^-$, optionally substituted alkyl aryl, or $R^{33}$ and $R^{34}$, $R^{34}$ and $R^{35}$, and/or $R^{35}$ and $R^{36}$ taken together form an optionally substituted fused ring having 6 atoms (preferably a sulfonated carbocyclic or heterocyclic ring);
Y is —O— or —N(Y$^1$)— where Y$^1$ is —CH$_2$-Z, activated lower alkyl or optionally substituted arlkyl;

including the a single stereoisomers, mixture of stereoisomers, solvates, probe-, target- and/or support-conjugates thereof.

In another aspect or the compounds of Formula I and/or D2, at least one of $R^{21}$ to $R^{36}$ is joined to L1, L2 or FETL via an arylene or aralkylene moiety (preferably phenylene, benzyl, naphthalene, or naphthalenyl-methyl).

The fluorescence energy transfer linkers (FETL) of the invention include those represented by the formulae:

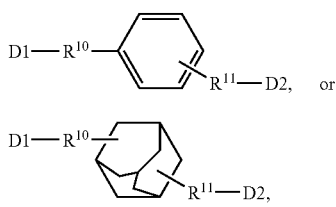
FETL1

FETL2 where:
$R^{10}$ is D1-C(O)—, D1-N(H)—CH$_2$—, D1-S—C(O)—, D1-O—C(S)— or D1-S—CH$_2$—; and
$R^{11}$ is —C(O)-D2, —CH$_2$—N(H)-D2; —C(O)—S-D2, —C(S)—O-D2 or CH$_2$—S-D2;

where:
q is zero or 1;
$R^{12}$ is H, halo, or optionally substituted-alkyl, -alkenyl, -alkynyl or -aryl;
$R^{13}$ is H, SO$_3^-$ or optionally substituted-alkyl, -alkenyl, -alkynyl or -aryl; and
$R^{14}$ is a secondary or tertiary amine or heterocyclyl, particularly N(H) or piperazine.

Still another aspect entails the compounds of Formula I and/or D2 where at least one of $R^{21}$ to $R^{36}$ is joined to L1, L2 or FETL via an arylene or aralkylene moiety (preferably phenylene, benzyl, naphthalene, or naphthalenyl-methyl).

Yet another aspect of the compounds of the invention pertains to a fluorescence energy transfer dye represented by Formula II:

Probe-L1-(D1 or D2)-FETL-(low affinity false target)   (Formula II)

where:
Probe, D1, D2 and FETL are as defined above;
L1 is a link for attachment to a the Probe; and
low affinity false target is an analyte for the Probe disposed to deactivate, block or otherwise prevent coupling of FETL to a corresponding D2 or D1 until said low affinity false target is displaced by a higher affinity true target.

Another aspect of the invention pertains to compositions of the formulae: Probe-L1-(D1 or D2), Probe-L1-(D1 or D2)-FETL, Probe-L1-(D1 or D2)-FETL-(D2 or D1)-L2-SolidSupport, and SolidSupport-L1-(D1 or D2)-FETL-(D2 or D1)-L2-Probe, where
the Probe is a polynucleotide (complementary DNA, DNA intercalators, RNA, optionally provided in liposomal formulation for cell permeation), an antibody, a triglyceride, a low density lipoprotein or a lectin,
and the Probe is addressed to a target substance, such as a cell, cell fragment, cell surface marker (e.g., a T cell receptor), a polynucleotide sequence (e.g., a DNA sequence or RNA sequence), or the like.

Yet another aspect of the invention pertains to multi-color fluorescence energy transfer dye sets, in which the excitation spectra fall within about 20 nm of each other, while the emission spectra are separated by about 30 to 60 nm, such as GUAVA I, GUAVA V PD590, TAM-XY-GY5, and GUAVA III-5-carboxy GYZ760, each of which can be excited at 532 nm and emit, respectively, at 570 nm, 630 nm, 670 nm and 760 nm.

The invention also provides novel assays, including assays requiring no pre-analysis purification for removal of unbound dye, and proximity assays. The compounds of the invention and other fluorescent dyes and dye couples can be employed in the methods of the invention.

An assay requiring no pre-analysis purification for removal of unbound dye, includes the steps of either:

(a) in a suitable assay vessel, contacting a substance to be tested and a Probe1-L1-D1 conjugate that is site-specific for a first epitope on a target;

(b) introducing a Probe2-L2-D2 conjugate to the vessel, where said Probe2 is site-specific for bound Probe 1 or for a second epitope spatially proximate to the first epitope;

(c) causing D1 to absorb energy; and (d) measuring the level of D2 emission, or the steps of:

(e) contacting a substance to be tested and a target site specific Probe-L1-(D1 or D2)-FETL-(low affinity false target) conjugate in a suitable assay vessel under conditions suitable for preferential binding of the Probe to the target site, as opposed to the low affinity false target;

(f) introducing a D2 or D1 fluorescence energy transfer dye having an activated site for coupling to the FETL into the vessel, under conditions suitable for coupling to FETL where the low affinity false target is not bound to the Probe;

(g) causing D1 to absorb energy; and (h) measuring the level of D2 emission.

An assay for determining the proximity as between two target sites on a substance of interest includes the steps of:

(a) contacting a substance to be tested and a target-site-specific donor dye in a suitable assay vessle;

(b) introducing a target-site-specific reporter dye into the vessel, where the reporter dye's target is either spatially proximate to the donor dye's target or is specific for a given target to be tested for spatial proximity to the donor dye's target, and the reporter dye's energy absorption spectra overlaps the emission spectra of the donor dye;

(c) causing the donor dye to absorb energy; and (d) measuring the level of reporter dye emission.

in a multiplexed embodiment of this assay:

step (b) further includes introducing two or more target-site-specific reporter dyes into the vessel, the reporter dyes having overlapping energy absorption spectra, distinct emission spectra, and having different targets to be tested for spatial proximity to the donor dye's target; and step (d) further includes measuring the level of reporter dye emission at the wavelengths characteristic of such reporter dyes.

These and other aspects are desecribed in greater detail in the following detailed description of the invention, the examples and claims.

DETAILED DESCRIPTION OF THE INVENTION

Definitions

As used in the present specification, the following words and phrases are generally intended to have the meanings as set forth below, except to the extent that the context in which they are used indicates otherwise. The following abbreviations and terms have the indicated meanings throughout:

Ac=acetyl
B=biotin
DIEA=di-isopropylethyl amine
DMF=N,N-dimethylformamide
DMSO=dimethyl sulfoxide
Et=ethyl
Ph=phenyl
SA=strepavidin The terms "activated" or "activating," for example, as used in connection with any of the terms "group," "alkyl group" or "carboxylic acid ester," refers to such groups including a reactive moiety useful for labeling (or attachment) to other molecules (e.g., having available amino, hydroxy and/or sulfhydryl groups). Exemplary reactive moieties include such groups containing isothiocyanate, isocyanate, monochlorotriazine, dichlorotriazine, mono- or di-halogen substituted pyridine, mono- or di-halo substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)proprionamide, glyoxal and aldehyde.

The term "alkenyl" refers to the monoradical branched or unbranched, unsaturated or polyunsaturated hydrocarbon chain, having from about 2 to 20 carbon atoms, more preferably about 2 to 10 carbon atoms. This term is exemplified by groups such as ethenyl, but-2-enyl, and the like.

The term "alkyl" refers to a monoradical branched or unbranched saturated hydrocarbon chain preferably having from about 1 to 20 carbon atoms, more preferably about 1 to 10 carbon atoms, and even more preferably about 1 to 6 carbon atoms. This term is exemplified by groups such as methyl, ethyl, n-propyl, iso-propyl, n-butyl, iso-butyl, n-hexyl, n-decyl, tetradecyl, and the like. "Lower alkyl" except where otherwise recited in connection with a specific range of carbon atoms, typically refers to an alkyl group having about 1 to 8 carbon atoms.

The term "substituted alkyl" refers to an alkyl group in which 1 or more (up to about 5, preferably up to about 3) hydrogen atoms is replaced by a substituent independently selected from the group: =O, =S, acyl, acyloxy, optionally substituted alkoxy, optionally substituted amino, azido, carboxyl, (optionally substituted alkoxy)carbonyl, (optionally substituted amino)carbonyl, cyano, optionally substituted cycloalkyl, optionally substituted cycloalkenyl, halogen, hydroxyl, nitro, sulfanyl, sulfinyl, and sulfonyl.

The term "alkylene" refers to a diradical derived from the above-defined monoradical, alkyl. This term is exemplified by groups such as methylene (—$CH_2$—), ethylene (—$CH_2CH_2$—), the propylene isomers [e.g., —$CH_2CH_2CH_2$— and —$CH(CH_3)CH_2$—] and the like.

The term "amide" refers to compounds containing one or more acyl group attached to a nitrogen. Amides derived from carbon acids may be termed "carboxamides", those from sulfonic acids "sulfonamides."

The term "amino acid" includes both natural amino acid and substituted amino acids. "Natural amino acid" refers to any of the twenty (20) common amino acids as generally accepted in the peptide art and represent L-amino acids unless otherwise designated (with the exception of achiral amino acids such as glycine). "Substituted amino acid" refers to an amino acid containing one or more additional chemical moieties that are not normally a part of the amino acid. Such substitutions can be introduced by a targeted derivatizing agent that is capable of reacting with selected side chains or terminal residues and via other art-accepted methods. For example, cysteinyl residues most commonly are reacted with alpha-haloacetates (and corresponding amines), such as chloroacetic acid or chloroacetamide, to give carboxymethyl or carboxyamidomethyl derivatives. Cysteinyl residues can also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Carboxyl side groups (aspartyl or glutamyl) can be selectively modified by reaction with carbodiimides such as 1-cyclohexyl-3-(2-morpholinyl-(4-ethyl) carbodiimide or 1-ethyl-3(4 azonia 4,4-dimethylpentyl) carbodiimide. Aspartyl and glutamyl residues can be converted to asparaginyl and glutaminyl residues by reaction with ammonium ions. Glutaminyl and asparaginyl residues can be deamidated to the corresponding glutamyl and aspartyl residues. Alternatively, these residues can be deamidated under mildly acidic conditions. Other modifications include hydroxylation of proline and lysine, phosphorylation of hydroxyl groups of seryl or theonyl residues, methylation of the alpha-amino groups of lysine, arginine and histidine side chains (see, e.g., T. E. Creighton, Proteins: Structure and Molecule Properties, W. H. Freeman & Co., San Francisco, pp. 79–86 (1983)), acetylation of the N-terminal amine, and amidation of C-terminal carboxyl groups.

The term "antibody" (interchangeably used in plural form) means an immunoglobulin molecule capable of specific binding to a target, such as a carbohydrate, polynucleotide or polypeptide, through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, humanized antibodies, chimeric antibodies, divalent antibodies, bispecific antibodies, and any other modified configuration of the immunoglobulin molecule that comprises an antigen recognition site of the required specificity. The antibody may include a mammalian heavy chain, which can be a mouse heavy-chain, rabbit heavy-chain, or human heavy-chain.

An "antigen" includes any substance that may be specifically bound by an antibody molecule. The term "antigen" encompasses biologic molecules including, but not limited to, simple intermediary metabolites, sugars, lipids, autoacids, hormones, as well as macromolecules such as complex carbohydrates, phospholipids, nucleic acids, and proteins.

The term "aromatic" refers to a cyclic or polycyclic moiety having a conjugated unsaturated $(4n+2)\pi$ electron system (where n is a positive integer), sometimes referred to as a delocalized π electron system.

The term "aryl" refers to an aromatic cyclic hydrocarbon group of from 6 to 20 carbon atoms having a single ring (e.g., phenyl) or multiple condensed (fused) rings (e.g., naphthyl or anthryl). Preferred aryls include phenyl, naphthyl and the like.

The term "substituted aryl" refers to an aryl group as defined above, which unless otherwise constrained by the definition for the aryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl. Preferred aryl substituents include alkyl, alkoxy, amino alkyl, carboxy, halo, trihalomethyl, and sulfonate.

The term "aralkyl" refers to the moiety "-alkylene-aryl" each having the meaning as defined herein. Such aralkyl groups are exemplified by benzyl, phenethyl, 3-naphthylpropenyl and the like.

The term "substituted aralkyl" refers to the moiety "-(optionally substituted aklylene)-(optionally substituted aryl)", each having the meaning as defined herein, where at least one of the aryl or alkylene groups is substituted, e.g., 4-(N-methyl-pyrrolyl)pentylene, 4-nitrobenzyl or 1-methoxycarbonyl-2-phenyl-ethyl.

The term "carbonyl" refers to the di-radical "—C(=O)—", also illustrated as "—C(O)—".

The term "(optionally substituted amino)carbonyl" refers to the group —C(O)-(optionally substituted amino). This moiety is also referred to as a primary, secondary or tertiary carboxamide.

The terms "carboxy," "carboxyl" and carboxylic acid refer to the moiety "—C(O)OH," also illustrated as "—COOH." The term is also intended to be interchangeable with carboxylic acid anion, i.e., "—COO" in such structures where the ionized form would be expected to exist in equilibrium with the acid. Similarly, the term "sulfonate" is meant to include "sulfonic acid".

The term "complementary sequence" is a single-stranded nucleic acid having the inverse and opposite sequence of nucleic acids from a target nucleic acid molecule.

The term "compound of Formula I" is intended to encompass the dyes, dye-linkers and dye couples of the invention as disclosed, and/or the salts of such compounds. In addition, the compounds of this invention include the tautomers, individual stereochemical isomers (arising from the selection of substituent groups) and mixtures of tautomers and/or isomers.

The term "cycloalkyl" refers to non-aromatic cyclic hydrocarbon groups of having about 3 to 40 (preferably about 4 to 15) carbon atoms having a single ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, cyclopentaphenanthren and the like.

The term "substituted cycloalkyl" refers to a cycloalkyl group substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocylooxy, hydroxyl, nitro, sulfanyl, sulfinyl, and sulfonyl.

The term "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

The term "epitope" means any chemical moiety that exhibits specific binding to an antibody. An "epitope" can also comprise an antigen, that is a moiety or molecule that contains an epitope, and, as such, also specifically binds to antibody. A single antigen molecule may contain multiple epitopes.

The terms "fluorescence energy transfer" ("FET") and "fluorescence resonance energy transfer" ("FRET") and "energy transfer" are used interchangeably.

The term "halo" or "halogen" refers to fluoro, chloro, bromo and iodo.

The term "heteroaryl" refers to an aromatic cyclic hydrocarbon group having about 1 to 40 (preferably from about 3 to 15) carbon atoms and about 1 to 10 heteroatoms (preferably about 1 to 4 heteroatoms, selected from nitrogen, sulfur, phosphorus, selenium and/or oxygen) within at least one ring. Such heteroaryl groups can have a single ring (e.g., pyridyl or furyl) or multiple condensed rings (e.g., indolizinyl or benzothienyl). Preferred heteroaryls include pyridyl, pyrrolyl, furyl, benzoimidazole, benzothiazole and benzoselenazol.

The term "substituted heteroaryl" refers to a heteroaryl group as defined above, which unless otherwise constrained by the definition for the heteroaryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino) carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocylooxy, hydroxyl, nitro, sulfanyl, sulfinyl, and sulfonyl.

The term "heteroaralkyl" refers to the moiety "-alkylene-heteroaryl" each having the meaning as defined herein.

The term "substituted heteroaralkyl" refers to the moiety "-(optionally substituted aklylene)-(optionally substituted heteroaryl)", each having the meaning as defined herein.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenylene and the like.

The terms "heterocycle", "heterocyclic" and "heterocyclyl" refer to a monoradical, saturated or unsaturated, non-aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, and/or oxygen) within the ring. Such heterocyclic groups can have a single ring or multiple condensed rings. Preferred heterocyclics include morpholino, piperidinyl, and the like.

The terms "substituted heterocycle", "substituted heterocyclic" and "substituted heterocyclyl" refer to a heterocyclyl group as defined above, which unless otherwise constrained by the definition for the heterocycle, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocylooxy, hydroxyl, nitro, sulfanyl, sulfinyl, and sulfonyl.

The term "heterocycloalkyl" refers to the moiety "-alkylene-heterocycle" each having the meaning as defined herein.

The term "substituted heterocycloalkyl" refers to the moiety "-(optionally substituted aklylene)-(optionally substituted heterocycle)", each having the meaning as defined herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns (e.g., substituted alkyl can include alkyl substituted with optionally substituted cycloalkyl groups, which in turn can be substituted with optionally substituted alkyl, potentially ad infinitum) that are sterically impractical and/or synthetically non-feasible.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. It is understood that the double stranded polynucleotide sequences described herein also include the modifications described herein. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P—NH$_2$), a mixed phosphoramidate-phosphodiester oligomer, or a peptide backbone (PNA). A phosphorothioate linkage can be used in place of a phosphodiester linkage. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers.

The term "probe" (or "analyte binding molecule") refers to a targeting moiety for selectively binding with at least one targeting site on a substance to be tested, for example, through covalent bonds, ionic bonds, dispersion forces, hydrogen bonding, or antibody-antigen interactions. The nature of the probe will depend upon the nature of the substance to be tested, including, for example, a carbohydrate, nucleic acid, polypeptide, lipid, or phospholipid. The probe can be any molecule capable of binding to a target or analyte binding site and to a donor or reporter molecule as applicable. Examples of probes that can be used include polynucleotides (complementary DNA, DNA intercalators, RNA, optionally provided in liposomal formulation for cell permeation), antibodies, triglycerides, low density lipoproteins, lectins.

The term "spatially proximate" means within distance allowing energy transfer from donor to reporter, i.e., within about 100 Angstroms (100 Å), preferably less than 70 Angstroms, more preferably less than 50 Angstroms, more preferably less than 30 Angstroms, more preferably less than 20 Angstroms.

The term "substance to be tested" refers to a biological or chemical entity that can be detected via binding to a compound of the invention, including cells, cell fragments, polynucleotide sequences, antigens.

The term "sulfanyl" refers to the groups: —S-(optionally substituted alkyl), —S-(optionally substituted aryl), —S-(optionally substituted heteroaryl), —S-(optionally substituted heterocyclyl).

The term "sulfinyl" refers to the groups: —S(O)-(optionally substituted alkyl), —S(O)-optionally substituted aryl), —S(O)-(optionally substituted heteroaryl), —S(O)-(optionally substituted heterocyclyl).

The term "sulfonyl" refers to the groups: —S(O$_2$)-(optionally substituted alkyl), —S(O$_2$)-optionally substituted aryl), —S(O$_2$)-(optionally substituted heteroaryl), —S(O$_2$)-(optionally substituted heterocyclyl).

The term "sulfonic acid" is meant to include its ionized form "sulfonate" and its salts (e.g., K, Na, and NH$_4$)

The term "target" or "analyte binding site" refers to a portion of a substance to be tested, which is typically uniquely characteristic of such substance, such as a cell, cell fragment, cell surface marker (e.g., a T cell receptor), a polynucleotide sequence (e.g., a DNA sequence or RNA sequence), or the like.

Compounds of the Present Invention

The present invention provides certain fluorescent dyes, dye linkers and dye couples, for example as represented by Formula I:

-L1-D1-FETL-D2-L2-   (Formula I)

where:
L1 is a link for attachment to a probe or target, for attachment to a solid support, or is absent;
L2 is a link for attachment to a probe or target, for attachment to a solid support, or is absent; and
FETL is a fluorescence energy transfer linker comprising a symmetric, rigid or sterically hindered, divalent moiety joined to D1 and D2 via an amine, carbonyl, activated carboxylic acid ester, disulfide, thiol or thiol ester;

D1 is a donor dye represented by the formula:

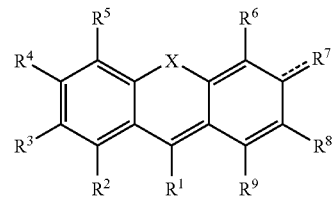

where:
X is O or C(R*R**), where R* and R** are independently lower alkyl or —CH$_2$-Z;
$R^1$ is H, CF$_3$, perfluoropropyl, lower alkyl acid, substituted aryl (preferably 5–6 membered mono or 10–12 membered fused, esp. o-benzoic acid), substituted heteroaryl (5–6 membered mono or 10–12 membered fused) or Z;
$R^2$ is H, halo, SO$_3^-$, or is taken together with $R^3$ to form an optionally substituted fused ring having 5 to 7 atoms (preferably a 6-membered aryl ring);
$R^3$ is halo (preferably chloro), Z, or is taken together with $R^2$ and/or $R^4$ to form an optionally substituted fused ring having 5 to 7 atoms (preferably a 6-membered ring);
$R^4$ is =O or OH, —N($R^{4'}R^{4''}$) or =N$^+$($R^{4'}R^{4''}$), or is taken together with $R^3$ and/or $R^5$ to form an optionally substituted fused ring having 5 to 7 atoms (preferably a 6-membered ring),
where $R^{4'}$ is H, lower alkyl or L1, and
$R^{4''}$ is H, lower alkyl or CH$_2$-Z;
$R^5$ is H, halo, Z, or is taken together with $R^4$ to form an optionally substituted fused ring having 5 to 7 atoms (preferably a 6-membered ring);
$R^6$ is H, halo, Z, or is taken together with $R^7$ to form an optionally substituted fused ring having 5 to 7 atoms (preferably a 6-membered ring);
$R^7$ is =O or OH, —N($R^{7'}R^{7''}$) or =N$^+$($R^{7'}R^{7''}$), or is taken together with $R^6$ and/or $R^8$ to form an optionally substituted fused ring having 5 to 7 atoms (preferably a 6-membered ring),
where $R^{7'}$ is H, lower alkyl or L1, and
$R^{7''}$ is H, lower alkyl or CH$_2$-Z;
$R^8$ is halo (preferably chloro), Z, or is taken together with $R^7$ and/or $R^9$ to form an optionally substituted fused ring having 5 to 7 atoms (preferably a 6-membered ring);
$R^9$ is H, halo, SO$_3^-$, or is taken together with $R^8$ to form an optionally substituted fused ring having 5 to 7 atoms (preferably a 6-membered aryl ring); and
Z is a group of the formula: -Z*-Z$^1$-(L1, L2 or FETL), where:
Z* is methylene, methoxy, ethoxy, aminomethyl, aminoethyl, aminopropynyl, aminobutynyl, carboxyethenyl, carboxyethynyl, optionally substituted aryl or optionally substituted heteroaryl;
Z$^1$ is —C(O)—, —N(Z$^2$)-, —CH$_2$—O—, —CH$_2$—C(O)—, —CH$_2$—N(Z$^2$)-, —CH$_2$—S—, —CH$_2$—S(O)—, —CH$_2$—S(O$_2$)— or is absent; and
Z$^2$ is H, C$_1$ to C$_8$ optionally substituted lower alkyl, or optionally substituted aryl; (substituents preferably SO$_3^-$, COOH, NH$_2$, CH$_2$NH$_2$, SH, SCH$_3$)

D2 is an acceptor/reporter dye represented by formula D1 or by a formula of the group:

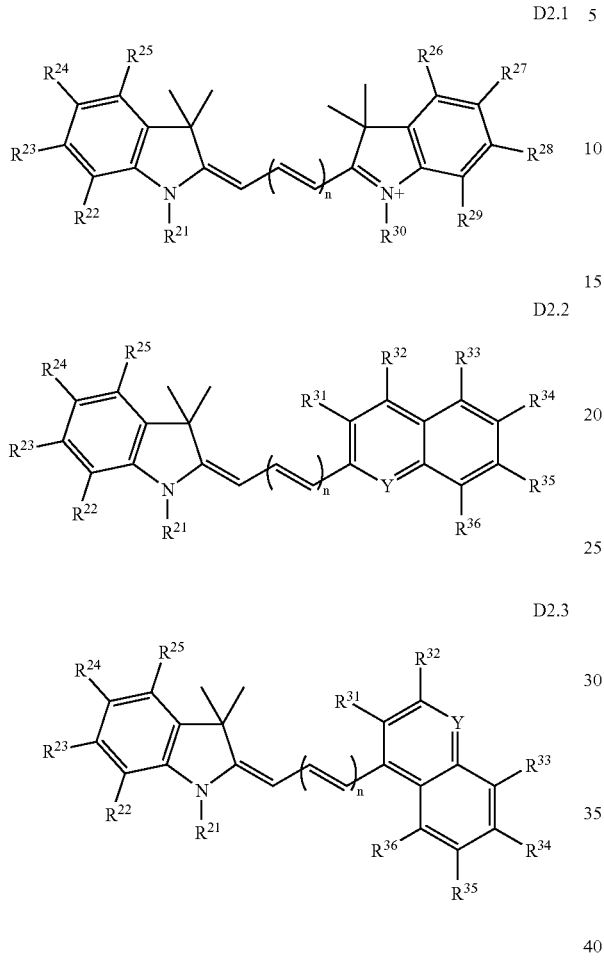

where:
- at least one of $R^{21}$ to $R^{36}$ is joined to FETL,
- n is zero, 1, 2 or 3;
- $R^{21}$ and $R^{30}$ are independently —CH$_2$-Z, activated lower alkyl, or optionally substituted aralkyl;
- $R^{22}$ to $R^{29}$ are independently H, SO$_3^-$, or optionally substituted alkyl, or $R^{22}$ and $R^{23}$, $R^{23}$ and $R^{24}$, $R^{24}$ and $R^{25}$, $R^{26}$ and $R^{27}$, $R^{27}$ and $R^{28}$ and/or $R^{28}$ and $R^{29}$ taken together form an optionally substituted fused ring having 6 atoms (preferably sulfonated aryl ring); and
- $R^{31}$ and $R^{32}$ are independently H, optionally substituted alkyl, aryl, or taken together form an optionally substituted fused ring having 6 atoms (preferably sulfonated carbocyclic or heterocyclic ring);
- $R^{33}$ to $R^{36}$ are independently H, SO$_3^-$, optionally substituted alkyl, aryl, or $R^{33}$ and $R^{34}$, $R^{34}$ and $R^{35}$, and/or $R^{35}$ and $R^{36}$ taken together form an optionally substituted fused ring having 6 atoms (preferably a sulfonated carbocyclic or heterocyclic ring);
- Y is —O— or —N(Y$^1$)— where Y$^1$ is —CH$_2$-Z, activated lower alkyl, or optionally substituted arlkyl;

including the a single stereoisomers, mixture of stereoisomers, solvates, probe-, target- and/or support-conjugates thereof.

In addition to the foregoing, various public domain acceptor/reporter dyes can be employed as D2, such as D2.4:

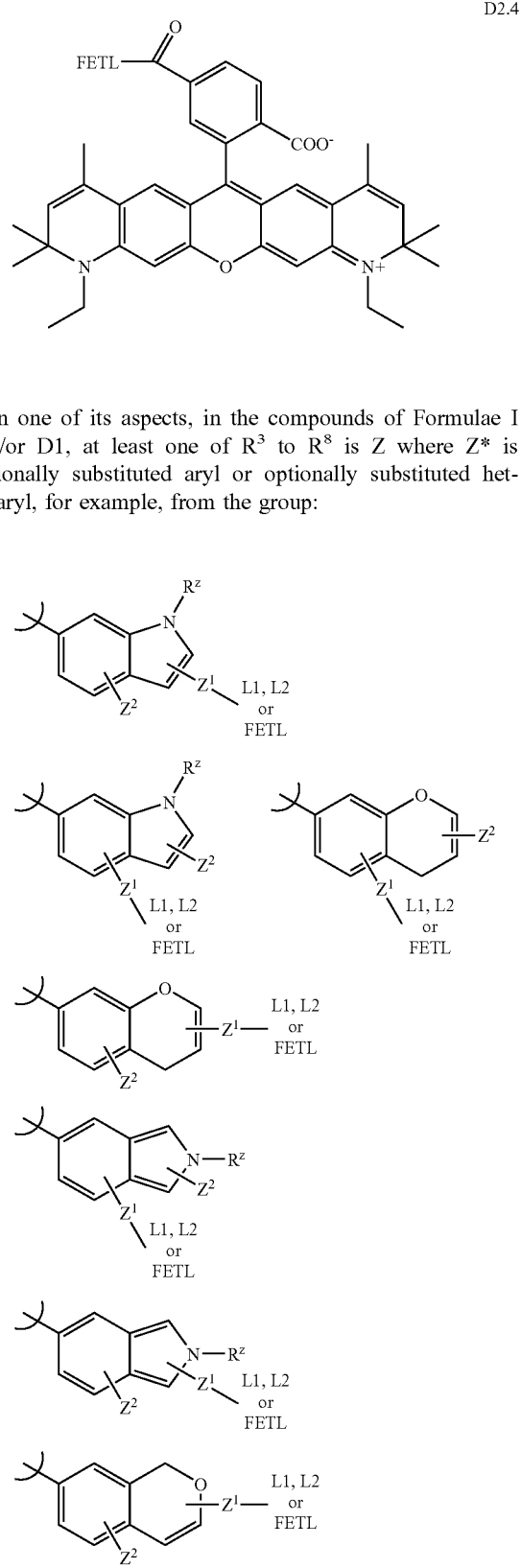

In one of its aspects, in the compounds of Formulae I and/or D1, at least one of $R^3$ to $R^8$ is Z where Z* is optionally substituted aryl or optionally substituted heteroaryl, for example, from the group:

-continued
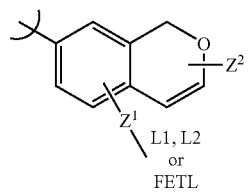
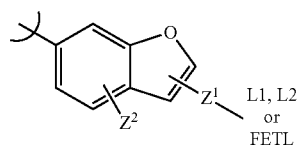
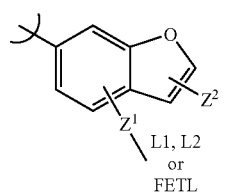
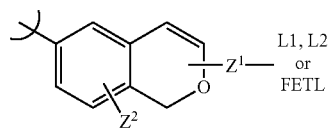
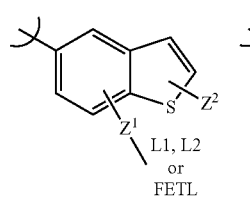
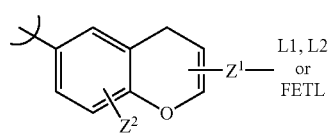
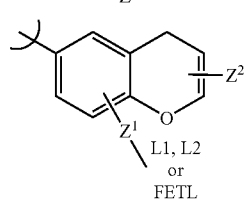
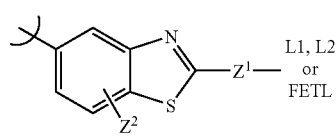
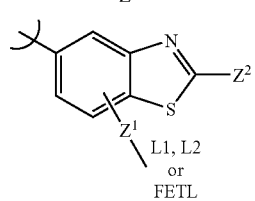
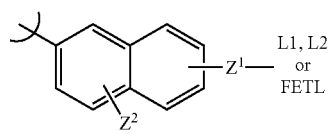
-continued
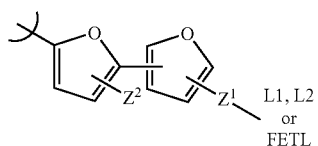
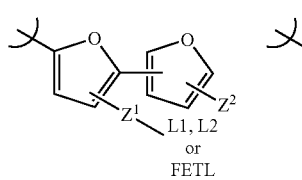
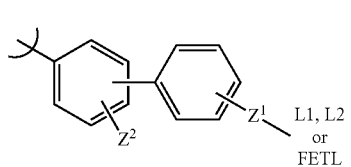
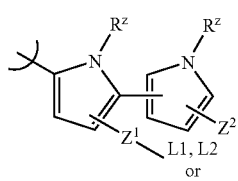
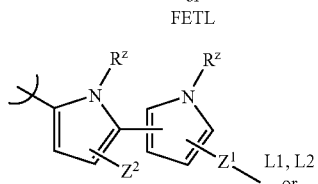
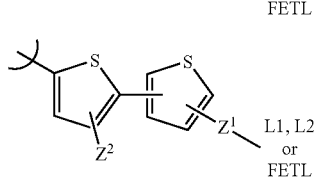
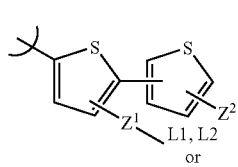
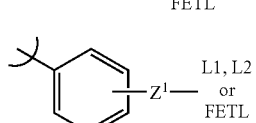
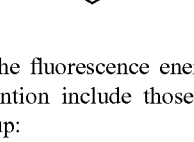
The fluorescence energy transfer linkers (FETL) of the invention include those represented by a formula of the group:
FETL1

-continued

FETL2

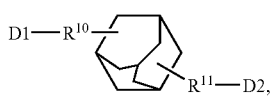

where:

R[10] is D1-C(O)—, D1-N(H)—CH$_2$—, D1-S—C(O)—, D1-O—C(S)— or D1-S—CH$_2$—; and

R[11] is —C(O)-D2, —CH$_2$—N(H)-D2; —C(O)—S-D2, —C(S)—O-D2 or CH$_2$—S-D2;

FETL3

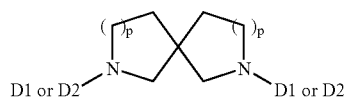

where:

p is independently 0, 1, 2 or 3; and

FETL4

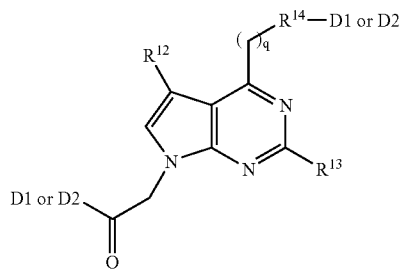

where:

q is zero or 1;

R[12] is H, halo, or optionally substituted-alkyl, -alkenyl, -alkynyl or -aryl;

R[13] is H, SO$_3$[−] or optionally substituted-alkyl, -alkenyl, -alkynyl or -aryl; and R[14] is a secondary or tertiary amine or heterocyclyl, particularly N(H) or piperazine.

In another aspect, for example, involving the novel methods of the invention or compounds of the invention where FETL is FETL3 or FETL4 and/or in the compounds of Formula I and/or D2 where at least one of R[21] to R[36] is joined to L1, L2 or FETL via an arylene or aralkylene moiety (preferably phenylene, benzyl, naphthalene, or naphthalenyl-methyl), each Z* can additionally be selected from:

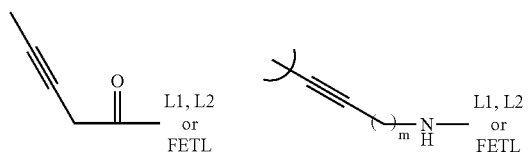

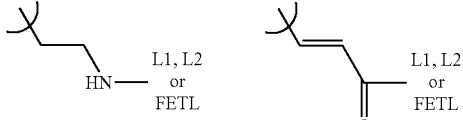

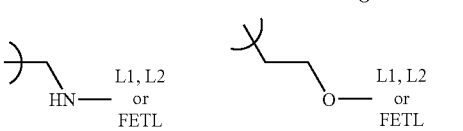

Still another aspect entails the compounds of Formula I and/or D2 where at least one of R[21] to R[36] is joined to L1, L2 or FETL via an arylene or aralkylene moiety (preferably phenylene, benzyl, naphthalene, or naphthalenyl-methyl).

Yet another aspect of the compounds of the invention pertains to a fluorescence energy transfer dye represented by Formula II:

Probe-L1-(D1 or D2)-FETL-(low affinity false target)  (Formula II)

where:

Probe, D1, D2 and FETL are as defined above;

L1 is a link for attachment to a the Probe; and low affinity false target is an analyte for the Probe disposed to deactivate, block or otherwise prevent coupling of FETL to a corresponding D2 or D1 until said low affinity false target is displaced by a higher affinity true target.

Another aspect of the invention pertains to compositions of the formulae: Probe-L1-(D1 or D2), Probe-L1-(D1 or D2)-FETL, Probe-L1-(D1 or D2)-FETL-(D2 or D1)-L2-SolidSupport, and SolidSupport-L1-(D1 or D2)-FETL-(D2 or D1)-L2-Probe, where the Probe is a polynucleotide (complementary DNA, DNA intercalators, RNA, optionally provided in liposomal formulation for cell permeation), an antibody, a triglyceride, a low density lipoprotein or a lectin, and the Probe is addressed to a target substance, such as a cell, cell fragment, cell surface marker (e.g., a T cell receptor), a polynucleotide sequence (e.g., a DNA sequence or RNA sequence), or the like.

Yet another aspect of the invention pertains to multi-color fluorescence energy transfer dye sets, in which the excitation spectra fall within about 20 nm of each other, while the emission spectra are separated by about 30 to 60 nm, such as the GUAVA I, GUAVA V PD590, TAM-XY-GY5, GUAVA III-5-carboxy GYZ760 dye set shown below, each of which can be excited at 532 nm and emit, respectively, at 570 nm, 630 nm, 670 nm and 760 nm. Other such dye sets can be made using the compounds of the invention, as will be apparent to those skilled in the art in light of the present teachings.

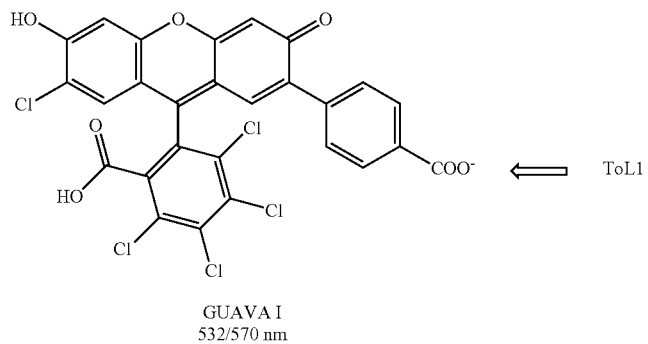
GUAVA I
532/570 nm
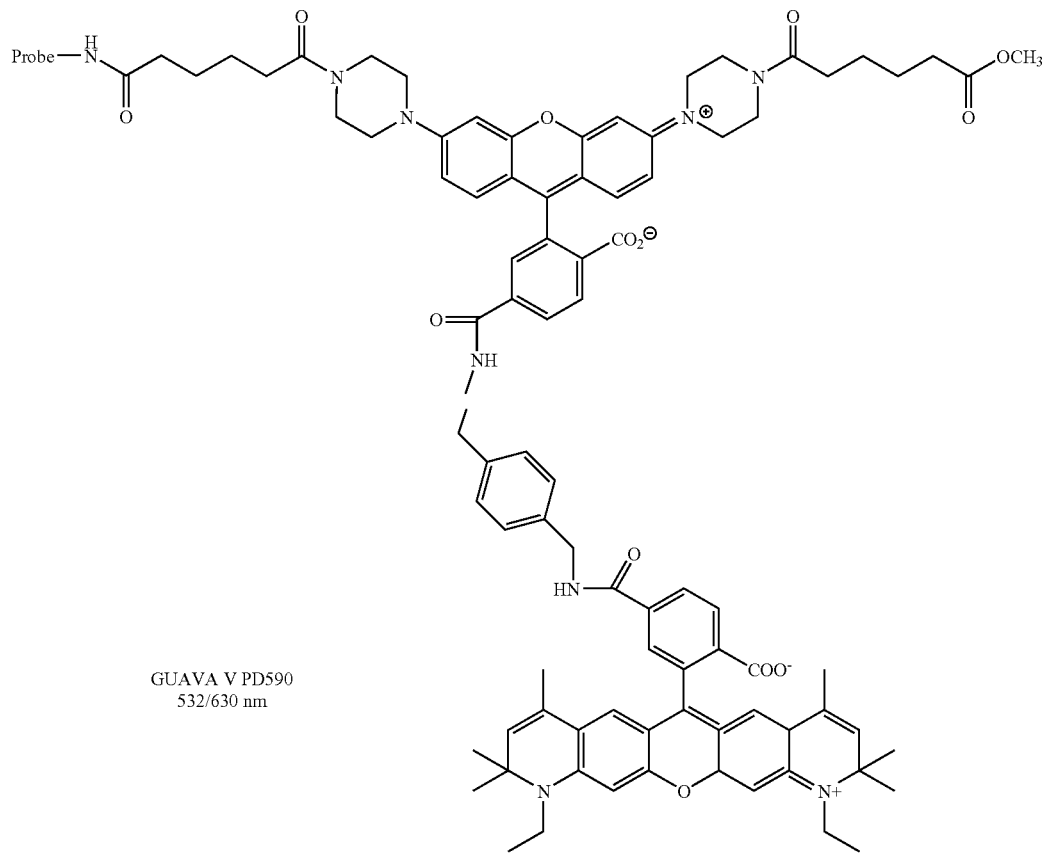
GUAVA V PD590
532/630 nm

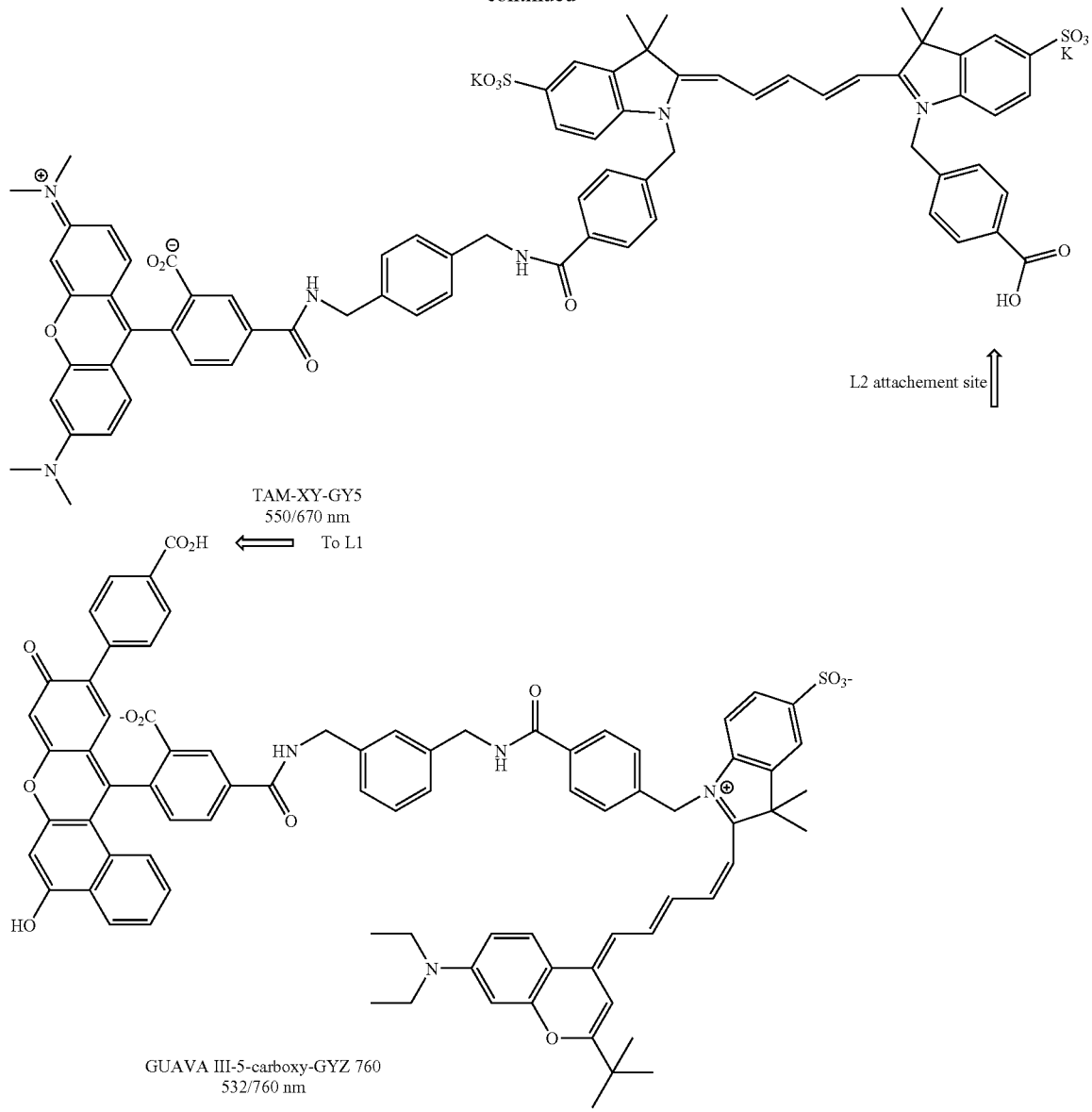

TAM-XY-GY5
550/670 nm

GUAVA III-5-carboxy-GYZ 760
532/760 nm

Nomenclature and Structures

The compounds of the present invention include fluorescent dyes as independent entities and as combined with one or more linking groups, other dyes, probes and/or targets. For the sake of simplicity, e.g., as illustrated above with reference to Formula D1 where Z is described as being a group of the formula "-Z*-$Z^1$-(L1, L2 or FETL)" the BOLD ITALICS have been employed in the specification and claims to indicate that while connected to Z at this position, neither L1, L2 nor FETL forms a part of the group "Z." In some instances, divalent moieties (e.g., methylene, 6-carboxy-naphthalenyl) are referred to by the name of their monovalent parent moieties (e.g., methyl, 6-carboxy-naphthyl), reflecting the nomenclature for such groups as employed in the names of the compounds of which they form a substituent (e.g., "—$CH_2$—$NH_3$" is an amino-methylene group, which would give rise to the nomenclature "amino-methyl" in the name of a compound).

The compounds can be named and numbered (e.g., using AutoNom version 2.1 in ISIS-DRAW or ChemDraw) as described below. For example, the following compound:

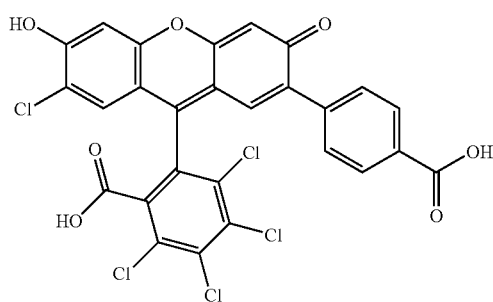

i.e., the compound according to Formula D1 where X is oxygen, $R^1$ is tetrachloro benzoic acid, $R^2$, $R^5$, $R^6$ and $R^9$ are hydrogen, $R^3$ is chloro, $R^4$ is hydroxy, $R^7$ is =O and $R^8$ is para-carboxyphenyl, can be named 2,3,4,5-tetrachloro-6-(2-(4'-carboxyphenyl)-7-chloro-6-hydroxy-3-oxo-3H-xanthen-9-yl)-benzoic acid; it can also be identified by the trivial name "GUAVA I".

Synthetic Reaction Parameters

Unless specified to the contrary, the reactions described herein take place at atmospheric pressure within a temperature range from 5° C. to 100° C. (preferably from 10° C. to 50° C.; most preferably at "room" or "ambient" temperature, e.g., 20° C.). Unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, preparative layer chromatography ("PLC") or a combination of these procedures. Specific illustrations of suitable separation and isolation procedures can be had by reference to the examples hereinbelow. However, other equivalent separation or isolation procedures can, of course, also be used.

Synthesis of the Compounds of Formula I

Syntheses of the compounds of Formula I are described below with reference to Reaction Schemes 1 to 8.

Reaction Scheme 1 illustrates synthesis of the compounds of Formula D1 where X is —O—.

Reaction Scheme 2 illustrates synthesis of the compounds of Formula D1 where X is —O— and $R^1$ is an optionally substituted ortho-benzoic acid.

Reaction Scheme 3 illustrates synthesis of the compounds of Formula D1 where X is —C(R*R**)— and is particularly suitable for those compounds where $R^4$ and $R^7$ are —N($R^{4'}R^{4''}$) and =N($R^{7'}R^{7''}$), respectively.

Reaction Scheme 4 illustrates synthesis of compounds of the Formula D1-FETL1.

Reaction Scheme 5 illustrates synthesis of D2.

Reaction Scheme 6 illustrates synthesis of FETL4.

Reaction Scheme 7 illustrates coupling of D1, FETL and D2.

Reaction Scheme 8 illustrates linking a compound of the invention to a biotinylated bead.

Starting Materials

The substituted phenols of Formulae 101 and 202, benzoic acids of Formula 102 and anhydrides of Formula 201 and other reactants are commercially available (e.g., from Aldrich Chemical Company, Milwaukee, Wis.) or can be readily prepared by those skilled in the art using commonly employed synthetic methodology.

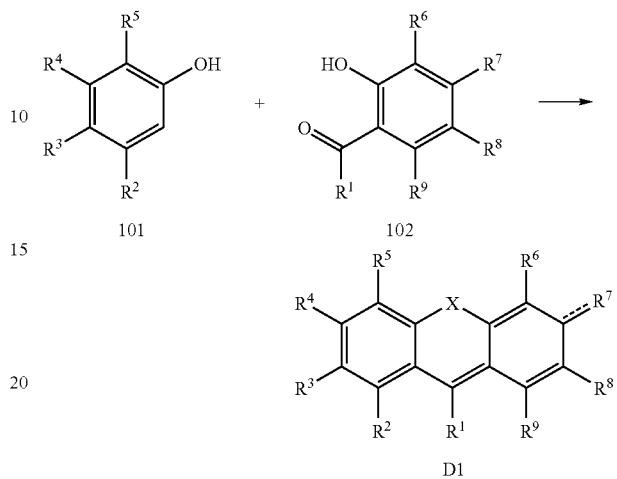

As illustrated in Reaction Scheme 1, a substituted phenol of Formula 101 is contacted with 1 eq. of a substituted ortho-hydroxy benzoic acid of Formula 102. The reaction takes place, e.g., in the presence of methanesulfonic acid, at an elevated temperature (130° C.) with stirring over a period of 2 hours. The reaction mixture is allowed to cool to room temperature and quenched by pouring into ice cold water. The crude product is extracted (e.g., with ethylacetate), washed, dried, concentrated and purified to give the corresponding compound of Formula I (where X is —O—).

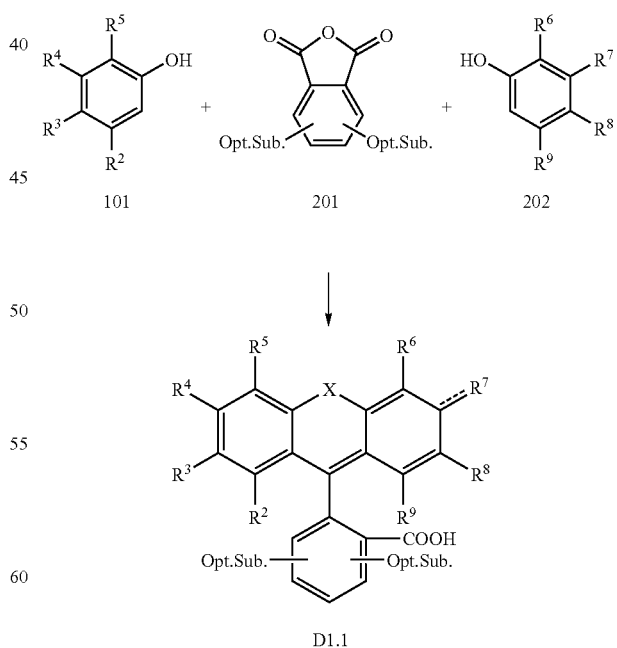

As illustrated in Reaction Scheme 2, an optionally substituted pthallic anhydride of Formula 201 is contacted with one molar equivalent each of substituted phenols 101 and 202 (or with 2 equivalents of 101 or 202 for synthesis of a symmetric product). The reaction takes place, e.g., in the presence of methanesulfonic acid, at an elevated temperature (130° C.) with stirring over a period of 2 hours. The reaction mixture is allowed to cool to room temperature and quenched by pouring into ice cold water. The crude product is extracted (e.g., with ethylacetate), washed, dried, concentrated and purified to give the corresponding compound of Formula I (where X is —O— and $R^1$ is an optionally substituted ortho-benzoic acid).

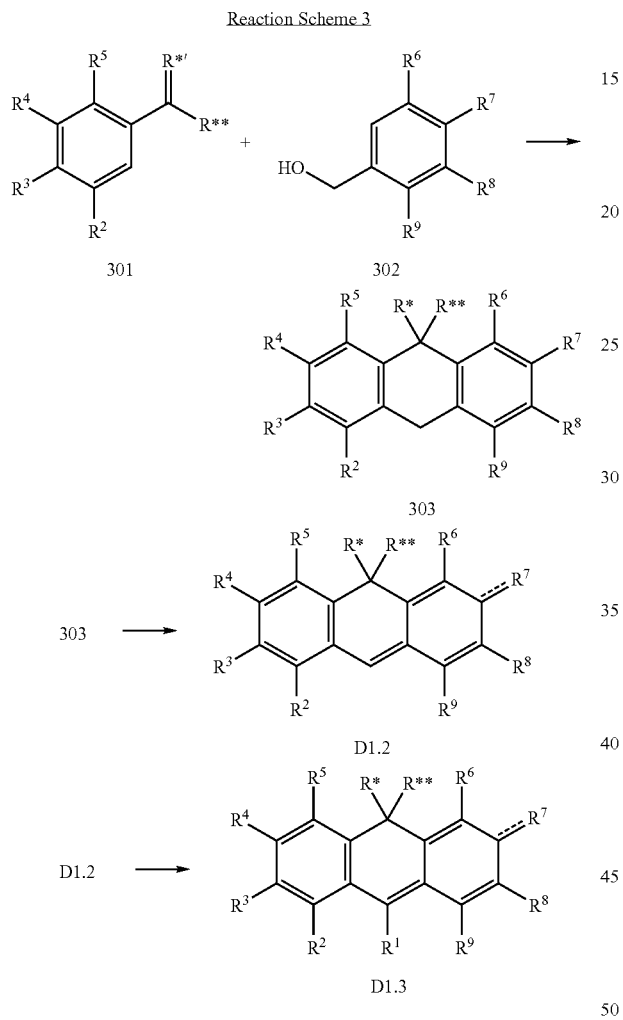

As illustrated in Reaction Scheme 3 compounds of Formula D1 where X is —C(R*R**)—, particularly those compounds where $R^4$ and $R^7$ are amines, can be obtained by dissolving a substituted isopropenyl phenyl compound of Formula 301 (where R*' is a precursor to R*) and a slight molar excess of a substituted phenyl methanol of Formula 302 in an organic solvent (such as DCM) at reduced temperature (e.g., in an ice bath). Boron trichloride is added dropwise and the reaction mixture is allowed to stir for 16 hours at room temperature; it is then cooled to −15° C. followed by the dropwise addition of concentrated sulfuric acid. The solvent is removed and the reaction mixture is allowed to stand at −4° C. for 16 hours. The resulting solution is poured into crushed ice and neutralized with NaOH to give the correspondingly substituted 9,10-dihydro-anthracene of Formula 303 as a residue that can be carried forward without further purification or isolation.

The residue (Formula 303) is taken up in a lower alkanol (e.g., ethanol) followed by the addition of perchloric acid and a molar equivalent of tetrabutyl-ammonium(meta)periodate. This reaction mixture is heated to reflux for 30 minutes, then is cooled to room temperature, poured into a solution of sodium perchlorate and allowed to stand for 16 hours to afford the corresponding 2,9-dihydro-anthracene of Formula D1.2 (i.e., a compound of Formula D1 where $R^1$ is H) as a solid precipitate that can be collected by filtration and dried.

To a large molar excess of an $R^1$-halide [e.g., 2-(4-bromophenyl)-4,4-dimethyl-2-oxazole] at reduced temperature (e.g., −78° C.) is added dropwise a compound of Formula D1.2 dissolved, e.g., in THF. The reaction takes place with stirring at −50° C. to −60° C. until completion (measured, e.g., by TLC) followed by quenching (e.g., with saturated ammonium chloride) extraction (e.g., with DCM) and purification (e.g., by column chromatography) to afford the corresponding $R^1$ substituted compound of Formula D1.3 (which, in the case of a benzoic acid $R^1$ group would remain protected by the oxazole group until deprotected with HCl in ethanol).

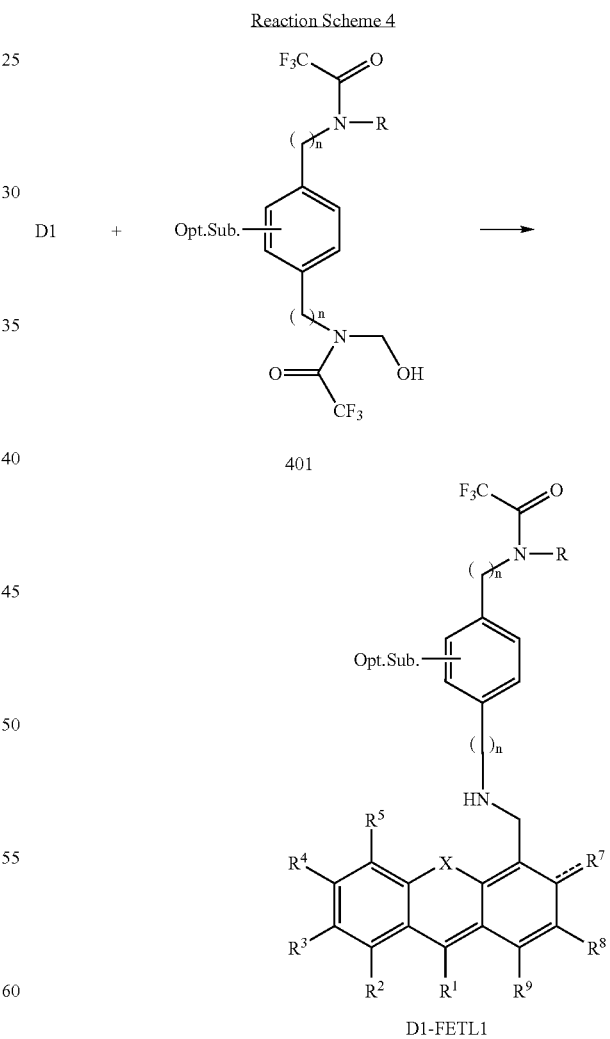

As illustrated in Reaction Scheme 4, a compound of Formula D1 where $R^6$ (or $R^5$) is hydrogen is contacted with one molar equivalent of an optionally substituted activated di-amino benzene of Formula 401 (where n is independently 0, 1 or 2, and R is H or alkyl) under reductive amination conditions (such as in the presence of $H_2SO_4$) to give the corresponding compound where $R^5$ or $R^6$ is Z-FETL (illustrated as FETL1).

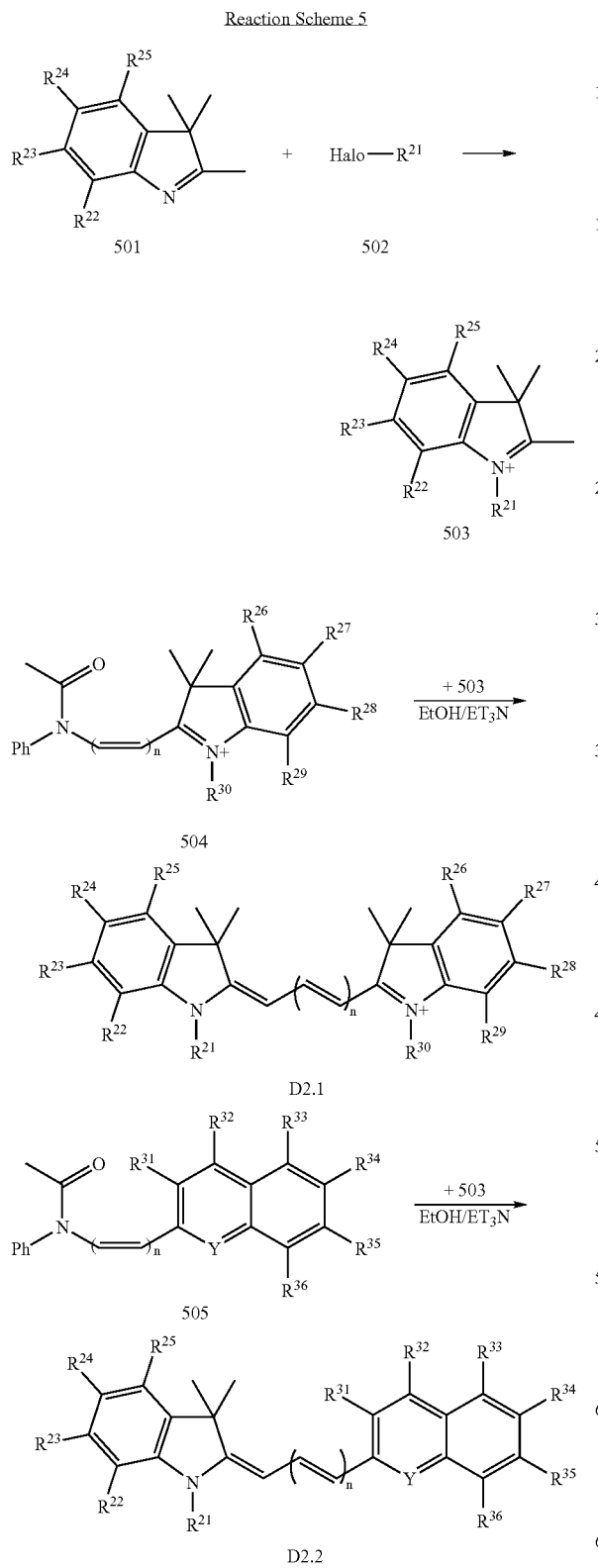

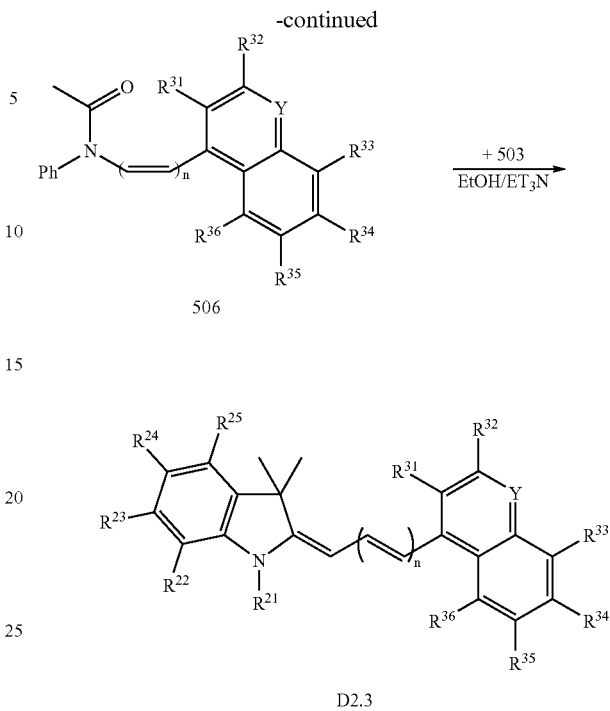

As illustrated in Reaction Scheme 5 an indole or benzoindole of Formula 501 can be N-derivatized by contact with a halogenated $R^{21}$ precursor of Formula 502. The reaction takes place, e.g., in ethanol with the addition of heat. $R^{21}$-substituted indole or benzindole of Formula 503 is then contacted with a (acetyl-phenyl-amino)-alkenyl-indole, -chromene or -quinoline of Formula 504, 505 or 506 (which can be $R^{30}$ or $Y^1$ substituted analogously to the preparation of Formula 503) to afford the corresponding compound of Formula D2.1, D2.2 or D2.3, respectively.

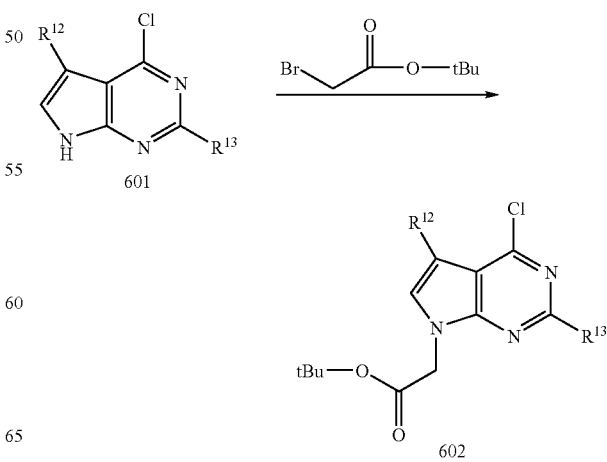

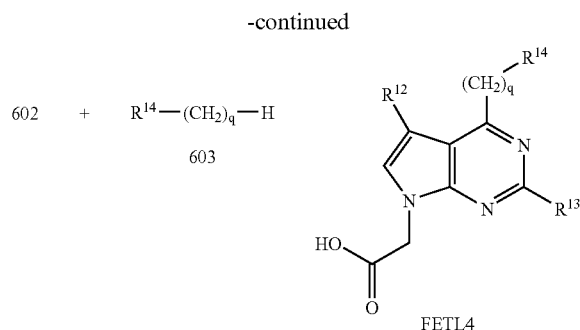

As illustrated in Reaction Scheme 6 compounds of Formula FETL4 can be prepared, for example, as described in Davol, J. *J. Chem. Soc.* 1960, 131, and in Lewis, A. F., Robins, R. K., *Can. J. Chem. Soc.* 1963, 41, 1807. In the example scheme shown above, a 4-chloro-7H-pryollo[2,3-d]pyrimidine is reacted with a bromo-acetate (such as 2-bromo-t-butyl acetate or 4-bromomethyl-benzoic acid methyl ester) in NaH/DMF to give the corresponding ester of Formula 602, to which can be add the substituent $(CH_2)_q$—$R^{14}$ by adding a compound of Formula 603 in DMF and converted to the corresponding acid with TFA/DCM to give the desired compound of FETL4.

FETL 3 can be synthesized, for example, as illustrated in U.S. Pat. No. 6,528,534.

As illustrated in Reaction Scheme 7 (top) a compound of Formula 701 (i.e., D1 having a pyrrolidine dione activating group) Formula 702 (i.e., FETL having two amine activating groups) and Formula 703 (i.e., D2 having a pyrrolidine dione activating group) are contacted together in a DMF/DIEA solvent to afford the corresponding FETL-linked dye couple of Formula I. The reaction can also be performed where the amine activating group is on D1 and/or D2 (as shown in the bottom reaction scheme), with corresponding pyrrolidine dione activating group(s) on Pre-FETL (identified as such to differentiate from the coupled linking group FETL).

As illustrated in Reaction Scheme 8, a dye couple of Formula I having a carboxylic acid attachment point for L2 is contacted with DCC/HOBT, strepavidin and biotinylated beads to afford labeled biotinylated beads corresponding to the formula D1-FETL-D2-L2-biotinylated bead (where L2 is SA:B).

Preferred Processes and Last Steps

A substituted phenol of Formula 101 is contacted with a substituted ortho-hydroxy benzoic acid of Formula 102 to give the corresponding compound of Formula D1 where X is O.

Compounds of Formula 701 and 702 (and optionally 703) are contacted in the presence of DMF/DIEA to give the corresponding compound of the formula D1-FETL or D1-FETL-D2.

Compounds of Formula 704 and 705 (and optionally 706) are contacted in the presence of DMF/DIEA to give the corresponding compound of the formula D1-FETL or D1-FETL-D2.

A compound of Formula I, such as D1-FETL-D2-COOH is contacted with strepavidin and a biotinylated bead to give the corresponding compound of the formula D1-FETL-D2-L2-(solid support) where L2 is strepavidin and the solid support is the biotinylated bead.

Preferred Compounds

Preferred for the compounds of the invention, and their methods of manufacture and use are the following combinations and permutations of substituent groups (sub-grouped, respectively, in increasing order of preference):

The compounds of Formula I.
  Where at least one of $R^3$ to $R^8$ is Z (i.e., $-Z^*-Z^1-$) where $Z^*$ is optionally substituted aryl or optionally substituted heteroaryl.
    Where $Z^*$ is optionally substituted aryl where aryl is phenyl, adamantyl, norboranyl, biphenyl or naphthyl.
      Where $Z^*$ is phenyl, biphenyl or naphthyl.
        Where $Z^1$ is COOH.
          Where $Z^*-Z^1$ is para-carboxy phenyl.
    Where $Z^*$ is optionally substituted heteroaryl where heteroaryl is furanyl, bifuranyl, thiophenyl, bithienyl, pyrrolyl, indolyl, isoindolyl, benzofuranyl, isobenzofuranyl, benzothiophenyl, benzothienyl, chromenyl and isochromenyl.
      Where $Z^*$ is chromenyl or isochromenyl.
        Where $Z^1$ is COOH.
  Where X is O.
  Where X is C(R*R**).
    Where R* and R** are lower alkyl.
      Where R* and R** are methyl.
        Where $R^4$ is $-N(R^{4'}R^{4''})$ and $R^7$ is $=N^+(R^{7'}R^{7''})$.
    Where $R^4$ is $-N(R^{4'}R^{4''})$ and $R^7$ is $=N^+(R^{7'}R^{7''})$.
  Where $R^1$ is $CF_3$, perfluoropropyl, lower alkyl acid or substituted aryl.
    Where $R^1$ is substituted aryl.
      Where $R^1$ is ortho-benzoic acid.
        Where $R^1$ is tetra-halo ortho-benzoic acid.
          Where $R^1$ is tetra-chloro ortho-benzoic acid.
        Where $R^1$ is tri-halo-(meta- or para-carboxy)-ortho-benzoic acid.
  Where $R^2$ is H or is taken together with $R^3$ to form a 6-membered aryl ring.
    Where $R^2$ is H.
  Where $R^3$ and/or $R^8$ are halo or Z.
    Where halo is chloro.
    Where $R^3$ is halo and $R^8$ is Z (i.e., $-Z^*-Z^1-$) where $Z^*$ is optionally substituted aryl or optionally substituted heteroaryl.
      Where $Z^*$ is optionally substituted aryl where aryl is phenyl, adamantyl, norboranyl, biphenyl or naphthyl.
        Where $Z^*$ is phenyl, biphenyl or naphthyl.
          Where $Z^1$ is COOH.
            Where $Z^*-Z^1$ is para-carboxy phenyl.
      Where $Z^*$ is optionally substituted heteroaryl where heteroaryl is furanyl, bifuranyl, thiophenyl, bithienyl, pyrrolyl, indolyl, isoindolyl, benzofuranyl, isobenzofuranyl, benzothiophenyl, benzothienyl, chromenyl and isochromenyl.
        Where $Z^*$ is chromenyl or isochromenyl.
          Where $Z^1$ is COOH.
    Where $R^3$ and $R^8$ are Z (i.e., $-Z^*-Z^1-$) where $Z^*$ is optionally substituted aryl or optionally substituted heteroaryl.
  Where $R^4$ is $=O$, OH, $-N(R^{4'}R^{4''})$ or $=N^+(R^{4'}R^{4''})$ and $R^7$ is $=O$, OH, $-N(R^{7'}R^{7''})$ or $=N^+(R^{7'}R^{7''})$.
    Where $R^4$ and $R^7$ are $=O$ or OH.
    Where $R^4$ is $-N(R^{4'}R^{4''})$ and $R^7$ is $=N^+(R^{7'}R^{7''})$.
  Where $R^5$ is H, halo or Z.
  Where $R^6$ is H, halo or Z.
  Where $R^9$ is H or is taken together with $R^8$ to form a 6-membered aryl ring.
    Where $R^9$ is H.
  Where FETL is FETL1 or FETL2.
    Where FETL is FETL1.
      Where $R^{10}$ and $R^{11}$ are D1-C(O)— or D1-N(H)—CH$_2$—.
        Where at least one of $R^3$ to $R^8$ is Z (i.e., $-Z^*-Z^1-$) where $Z^*$ is optionally substituted aryl or optionally substituted heteroaryl.
          Where $Z^*$ is optionally substituted aryl where aryl is phenyl, adamantyl, norboranyl, biphenyl or naphthyl.
            Where $Z^*$ is phenyl, biphenyl or naphthyl.
              Where $Z^1$ is COOH.
                Where $Z^*-Z^1$ is para-carboxy phenyl.
          Where $Z^*$ is optionally substituted heteroaryl where heteroaryl is furanyl, bifuranyl, thiophenyl, bithienyl, pyrrolyl, indolyl, isoindolyl, benzofuranyl, isobenzofuranyl, benzothiophenyl, benzothienyl, chromenyl and isochromenyl.
            Where $Z^*$ is chromenyl or isochromenyl.
              Where $Z^1$ is COOH.
        Where $R^2$ and $R^9$ are H.
        Where $R^3$ and/or $R^3$ are halo or Z.
          Where halo is chloro.
          Where $R^3$ is halo and $R^8$ is Z (i.e., $-Z^*-Z^1-$) where $Z^*$ is optionally substituted aryl or optionally substituted heteroaryl.
            Where $Z^*$ is optionally substituted aryl where aryl is phenyl, adamantyl, norboranyl, biphenyl or naphthyl.
              Where $Z^*$ is phenyl, biphenyl or naphthyl.
                Where $Z^1$ is COOH.
                  Where $Z^*-Z^1$ is para-carboxy phenyl.
          Where $R^3$ and $R^8$ are Z (i.e., $-Z^*-Z^1-$) where $Z^*$ is optionally substituted aryl or optionally substituted heteroaryl.
        Where $R^4$ is $=O$, OH, $-N(R^{4'}R^{4''})$ or $=N^+(R^{4'}R^{4''})$ and $R^7$ is $=O$, OH, $-N(R^{7'}R^{7''})$ or $=N^+(R^{7'}R^{7''})$.
      Where $R^{10}$ and $R^{11}$ are D1-C(O)— or D1-N(H)—CH$_2$—.
        Where at least one of $R^3$ to $R^8$ is Z (i.e., $-Z^*-Z^1-$) where $Z^*$ is optionally substituted aryl or optionally substituted heteroaryl.
          Where $Z^*$ is optionally substituted aryl where aryl is phenyl, adamantyl, norboranyl, biphenyl or naphthyl.
            Where $Z^*$ is phenyl, biphenyl or naphthyl.
              Where $Z^1$ is COOH.
                Where $Z^*-Z^1$ is para-carboxy phenyl.
          Where $Z^*$ is optionally substituted heteroaryl where heteroaryl is furanyl, bifuranyl, thiophenyl, bithienyl, pyrrolyl, indolyl, isoindolyl, benzofuranyl, isobenzofuranyl, benzothiophenyl, benzothienyl, chromenyl and isochromenyl.
            Where $Z^*$ is chromenyl or isochromenyl.
              Where $Z^1$ is COOH.
    Where at least one of $R^3$ to $R^8$ is Z (i.e., $-Z^*-Z^1-$) where $Z^*$ is optionally substituted aryl or optionally substituted heteroaryl.
      Where $Z^*$ is optionally substituted aryl where aryl is phenyl, adamantyl, norboranyl, biphenyl or naphthyl.
        Where $Z^*$ is phenyl, biphenyl or naphthyl.
          Where $Z^1$ is COOH.
            Where $Z^*-Z^1$ is para-carboxy phenyl.

Where Z* is optionally substituted heteroaryl where heteroaryl is furanyl, bifuranyl, thiophenyl, bithienyl, pyrrolyl, indolyl, isoindolyl, benzofuranyl, isobenzofuranyl, benzothiophenyl, benzothienyl, chromenyl and isochromenyl.
Where Z* is chromenyl or isochromenyl.
Where $Z^1$ is COOH.
Where FETL is FETL3 or FETL4.
Where FETL is FETL3
Where p is zero.
Where FETL is FETL4
Where q is 1
Where $R^{12}$ is H or optionally substituted aryl.
Where $R^{13}$ is H or optionally substituted aryl.
Where one of $R^{12}$ and $R^{13}$ is H and the other is Z-substituted aryl.
Where D2 is a dye of D1.
Where X and $R^1$ to $R^9$ are preferred as described above.
Where D2 is a dye of formula D2.1, D2.2 or D2.3.
Where $R^{21}$ $R^{30}$ and/or $Y^1$ is substituted aryl.
Where substituted aryl is carboxynaphthyl.
Where one or more of $R^{21}$ to $R^{36}$ is or bears a sulfonate.
Where n is 2.

Formula D1 where at least one of $R^3$ to $R^8$ is Z [i.e., -Z*-$Z^1$-(L1, L2 or FETL)] where Z* is optionally substituted aryl or optionally substituted heteroaryl. (It should be noted that L1, L2 and FETL do not form a part of the group "Z".)
Where Z* is optionally substituted aryl where aryl is phenyl, adamantyl, norboranyl, biphenyl or naphthyl.
Where Z* is phenyl, biphenyl or naphthyl.
Where $Z^1$ is COO-(L1, L2 or FETL).
Where Z*-$Z^1$ is para-carboxy phenyl.
Where Z* is optionally substituted heteroaryl where heteroaryl is furanyl, bifuranyl, thiophenyl, bithienyl, pyrrolyl, indolyl, isoindolyl, benzofuranyl, isobenzofuranyl, benzothiophenyl, benzothienyl, chromenyl and isochromenyl.
Where Z* is chromenyl or isochromenyl.
Where $Z^1$ is COOH.
Formula D2.1, D2.2 or D2.3.
Where $R^{21}$ $R^{30}$ and/or $Y^1$ is substituted aryl.
Where substituted aryl is carboxynaphthyl.
Where one or more of $R^{21}$ to $R^{36}$ is or bears a sulfonate.
Where n is 2.

Formula II where D1, D2 and FETL are preferred as described above with respect to Formula I.
Where the low affinity false target is a partial consensus polynucleotide sequence.
Where the low affinity false target is an antibody.
Where the low affinity false target is attached to the phenyl ring of FETL1.
Where the low affinity false target is a partial consensus polynucleotide sequence.
Where the low affinity false target is an antibody.

As illustrated with regard to the group of compounds where FETL in Formula I is FETL1, the above-described groups and sub-groups are individually preferred and can be combined to describe further preferred aspects of the invention.

One preferred subgroup of the compounds of the invention are those having one or more of the following substituents:

$R^1$ is H, $CF_3$, perfluoropropyl, lower alkyl acid, 5–6 membered mono or 10–12 membered fused substituted aryl or heteroaryl, or Z;
$R^2$ is H, halo, $SO_3^-$, or is taken together with $R^3$ to form an optionally substituted fused 6-membered aryl ring;
$R^3$ is halo, Z, or is taken together with $R^2$ and/or $R^4$ to form an optionally substituted fused 6-membered ring;
$R^4$ is =O or OH, —N($R^4R^{4"}$) or =$N^+(R^4R^{4"})$, or is taken together with $R^3$ and/or $R^5$ to form an optionally substituted fused 6-membered ring;
$R^5$ is H, halo, Z, or is taken together with $R^4$ to form an optionally substituted fused 6-membered ring;
$R^6$ is H, halo, Z, or is taken together with $R^7$ to form an optionally substituted fused 6-membered ring;
$R^7$ is =O or OH, —N($R^7R^{7"}$) or =$N^+(R^7R^{7"})$, or is taken together with $R^6$ and/or $R^8$ to form an optionally substituted fused 6-membered ring;
$R^8$ is halo, Z, or is taken together with $R^7$ and/or $R^9$ to form an optionally substituted fused 6-membered ring;
$R^9$ is H, halo, $SO_3^-$, or is taken together with $R^8$ to form an optionally substituted fused 6-membered aryl ring;
$R^4$ is —N($R^4R^{4"}$) or =$N^+(R^4R^{4"})$ and $R^7$ is —N($R^7R^{7"}$) or =$N^+(R^7R^{7"})$ when X is C($R^*R^{**}$);
Z is a group of the formula: -Z*-$Z^1$-(L1, L2 or FETL), where:
Z* is methylene, methoxy, ethoxy, aminomethyl, aminoethyl, aminopropynyl, aminobutynyl, carboxyethenyl, carboxyethynyl, optionally substituted aryl or optionally substituted heteroaryl,
$Z^1$ is —C(O)—, —N($Z^2$)-, —$CH_2$—O—, —$CH_2$—C(O)—, —$CH_2$—N($Z^2$)-, —$CH_2$—S—, —$CH_2$—S(O)—, —$CH_2$—S($O_2$)— or is absent, and
$Z^2$ is H, or is $C_1$ to $C_8$ lower alkyl or aryl optionally substituted with $SO_3^-$, COOH, $NH_2$, $CH_2NH_2$, SH, or $SCH_3$;
FETL comprises a symmetric, rigid or sterically hindered, divalent moiety joined to D1 and D2 via an amine, carbonyl, activated carboxylic acid ester, disulfide, thiol or thiol ester;
$R^{21}$ or $R^{30}$ is carboxy-naphthyl-methyl, mono- or di-ortho-substituted benzyl having an ortho-, meta- or para-carbonyl or activating group, or an activated $C_1$ to $C_6$ lower alkyl;
$R^{22}$ to $R^{29}$ are independently H, $SO_3^-$ or optionally substituted alkyl, or $R^{22}$ and $R^{23}$, $R^{23}$ and $R^{24}$, $R^{24}$ and $R^{25}$, $R^{26}$ and $R^{27}$, $R^{27}$ and $R^{28}$, and/or $R^{28}$ and $R^{29}$ taken together form a fused, sulfonated 6-membered aryl ring;
$R^{31}$ and $R^{32}$ are independently H, optionally substituted alkyl, aryl, or taken together form a fused, sulfonated 6-membered carbocyclic or heterocyclic ring;
$R^{33}$ to $R^{36}$ are independently H, $SO_3^-$, optionally substituted alkyl, aryl, or $R^{33}$ and $R^{34}$, $R^{34}$ and $R^{35}$, and/or $R^{35}$ and $R^{36}$ taken together form a fused, sulfonated 6-membered carbocyclic or heterocyclic ring; and/or
at least one of $R^{22}$ to $R^{29}$ or $R^{33}$ to $R^{36}$ is $SO_3^-$.

Further preferred is the subgroup of compounds of the invention having one or more of the following substituents:
$R^1$ is H, $CF_3$, perfluoropropyl, lower alkyl acid, an optionally substituted ortho-benzoic acid, or Z;
$R^2$ is H, halo or $SO_3^-$;
$R^3$ is halo or Z;
$R^4$ is =O or OH, —N($R^4R^{4"}$) or =$N^+(R^4R^{4"})$;
$R^5$ is H, halo or Z;
$R^6$ is H, halo or Z;
$R^7$ is =O or OH, —N($R^7R^{7"}$) or =$N^+(R^7R^{7"})$;
$R^8$ is Z;
$R^9$ is H, halo or $SO_3^-$;
Z is a group of the formula: -Z*-$Z^1$-(L1, L2 or FETL), where:

Z* is an optionally substituted aryl or heteroaryl of the group: phenyl, adamantyl, norboranyl, biphenyl, naphthyl, furanyl, bifuranyl, thiophenyl, bithienyl, pyrrolyl, indolyl, isoindolyl, benzofuranyl, isobenzofuranyl, benzothiophenyl, benzothienyl, chromenyl and isochromenyl, and $Z^1$ is —C(O)—, —N(H)—, —CH$_2$—O—, —CH$_2$—C(O)—, —CH$_2$—N(H)—, or is absent;

$R^{22}$ to $R^{29}$ are independently H, $SO_3^-$ or optionally substituted alkyl, or $R^{24}$ and $R^{25}$ and/or $R^{26}$ and $R^{27}$ taken together form a fused, sulfonated 6-membered aryl ring;

$R^{31}$ and $R^{32}$ are independently H, optionally substituted alkyl or aryl; and/or $R^{33}$ to $R^{36}$ are independently H, $SO_3^-$, optionally substituted alkyl or aryl.

General Utility

The compounds of the invention find use in a variety of applications. As will be appreciated by those in the art, the dyes according to Formulae D1 and D2 can be used individually and linked together (as in Formula I) via a fluorescence energy transfer linker as described with reference to FETL. Substances that can be detected/tested via attachment to the compounds of the invention are generally biological entities including cells, proteins, peptides, antibodies and sugars; non-biologic small molecules can also be detected. These compounds can be employed in any method or procedure in which fluoresecent dyes are known to be used, for example, including: flow cytometry, DNA sequencing, protein arrays, DNA arrays, immunoassays, capillary electrophoresis, HPLC, and as markers in fluorescence microscopy.

In particular, the donor and absorber/reporter dyes of the invention can be used in assays that do not require pre-analysis purification to remove unbound dye. In addition, the donor and absorber/reporter dyes of the invention can be employed in proximity assays to detect the presence of target sets of several proximate targets, and can be multiplexed to detect the relative proportions of several target sets.

Characterization and Testing

The dyes and linked dye couples of the invention are characterized primarily in terms of the wavelengths at which they absorb and emit light. These and other physical characteristics such as solubility, hydrophylicity and lipophilicity, stability and the like can be determined by conventional methodology, for example, NMR and HPLC. Suitability of the dyes, linked dye couples and labeled analytes for use in the methods of the invention can be determined, e.g., by fluorometric, spectrophotometric and chromatographic analysis, e.g., as described in U.S. Pat. No. 5,268,486.

Methods of the Invention

As will be appreciated by those skilled in the art, no specific instruction should be required to employ the dyes and linked dye couples of the invention in place of commercially available dyes in existing equipment and assays. Following are descriptions of an adaptation of conventional assay technique, which eliminates pre-analysis purification to remove unbound dye and of several proximity assays. It should be understood that the order in which the various assay components are employed can be changed as desired to fit a particular application.

An assay requiring no pre-analysis purification for removal of unbound dye can be performed in a suitable assay vessel as follows: (a) contact a substance to be tested and a Probe1-L1-D1 under conditions suitable for preferential binding of the Probe to a target site associated with the substance to be tested; (b) introduce a Probe2-L2-D2 to the test vessel under conditions suitable for preferential binding of Probe2 to bound Probe1 (as opposed to unbound Probe1) or to a second epitope within the target site, where D2 absorbs energy in the emission spectrum of D1 and D2 emits energy at a wavelength sufficiently removed to be measurable without interference from any other assay component (e.g., the absorption or emission D1); (c) causing D1 to absorb energy; and (d) measuring the level of D2 emission. Since unbound Probe1-L1-D1 and Probe2-L2-D2 will be free in solution, they will not be held sufficiently spatially proximate to to cause fluorescence by D2, thereby eliminating the need to remove unbound dye in a pre-analysis washing step.

Another assay requiring no pre-analysis purification for removal of unbound dye employs a Probe-L1-(D1 or D2)-FETL compound of the invention where the FETL is rendered unreactive in the absense of Probe1/target binding. This can be accomplished, for example, by attaching a low affinity false target for Probe1 to the FETL at or near its site for coupling to the second dye of a FET dye couple, thereby deactivating that site, sterically blocking or otherwise preventing coupling to the second dye until the low affinity false target is displaced by a higher affinity true target. The low affinity false target can bind to the Probe-L1-(D1 or D2)-FETL molecule of which it is a part, or can complex with other unbound Probe-L1-(D1 or D2)-FETL molecules in solution. Procedurally: (a) the Probe-L1-(D1 or D2)-FETL-(low affinity false target) is introduced to a suitable assay vessel and contacted with a substance to be tested under conditions suitable for preferential binding of Probe 1 to a target site associated with the substance to be tested, or in the absense of such a target bind to the low affinity false target; (b) introduce a D2 or D1 compound of the invention having an activated site for coupling to the FETL; (c) causing D1 to absorb energy; and (d) measuring the level of D2 emission. Here again, the unbound Probe-L1-(D1 or D2)-FETL and the complementary D2 or D1 will be free in solution, i.e., not held sufficiently spatially proximate to to cause fluorescence by D2, thereby eliminating the need to remove unbound dye in a pre-analysis washing step.

Generally, a proximity assay includes exposing an analyte to a donor dye molecule capable of attaching to a first binding site and a reporter dye molecule capable of attaching to a second binding site, exciting the donor molecule and monitoring for reporter molecule emission. If reporter molecule emission is detected, an analyte with spatially proximate first and second binding sites is present.

A proximity assay can be performed in a suitable assay vessel as follows: (a) contact a substance to be tested and a Probe1-L1-D1 conjugate (or a Probe1-L1-D1-FETL-D2 conjugate) under conditions suitable for preferential binding of Probe1 to a target site associated with the substance to be tested; (b) introduce a Probe2-L2-D2.1 conjugate to the test vessel under conditions suitable for preferential binding of Probe2 to a second target site of interest for its proximity to the first target, where D2.1 absorbs energy in the emission spectrum of D1 (or D2) and D2.1 emits energy at a wavelength sufficiently removed from the emission spectrum of D1 (or D2) to be measurable without interference from the emission of any other assay component (e.g., D1 or D2); (c) causing D1 to absorb energy; and (d) measuring the level of D2.1 emission. The level of D2.1 emission will correspond whether and the extent to which the second target site is spatially proximate to the first target site.

A multi-target proximity assay can be performed in a suitable assay vessel as follows: (a) contact a substance to be tested and a Probe1-L1-D1 conjugate (or a Probe1-L1-D1-FETL-D2 conjugate), under conditions suitable for preferential binding of Probe1 to a target site associated with the substance to be tested; (b) introduce a Probe2-L2-D2.1 conjugate and a Probe3-L2-D2.2 conjugate to the test vessel under conditions suitable for preferential binding of Probe2 and Probe 3 to a second and third target sites of interest for their proximity to the first target, where D2.1 and D2.2 absorb energy in the emission spectrum of D1 (or D2) and D2.1 and D2.2 emit energy at a wavelength sufficiently removed from the emission spectrum of D1 (or D2) and each other to be measurable without interference from any other assay component; (c) causing D1 to absorb energy; and (d) measuring the levels of D2.1 and D2.2 emission. The levels of D2.1 and D2.2 emission will correspond whether the second and third target sites are spatially proximate to the first target site and the relative proportions of the second and third target sites.

An alternative multi-target proximity assay can be performed in a suitable assay vessel as follows: (a) contact a substance to be tested and a series of conjugates such as Probe1-L1-D1, Probe2-L1-D1 and Probe3-L1-D1 under conditions suitable for preferential binding of Probes 1, 2 and 3 to target sites associated with the substance to be tested; (b) introduce a Probe4-L2-D2.1 conjugate, a Probe4-L2-D2.2 conjugate and a Probe4-L2-D2.3 conjugate to the test vessel under conditions suitable for preferential binding of Probe4 to a second target site of interest for its proximity to the first, second and third targets, where D2.1, D2.2 and D2.3 absorb energy in the emission spectrum of D1, and D2.1, D2.2 and D2.3 emit energy at wavelength sufficiently removed from the emission spectrum of D1 and each other to be measurable without interference from any other assay component; (c) causing D1 to absorb energy; and (d) measuring the levels of D2.1, D2.2 and D2.3 emission. The levels of D2.1, D2.2 and D2.3 emission will correspond whether the first, second and third target sites are spatially proximate to the fourth target site and the relative proportions of the first, second and third target sites. Those skilled in the art will appreciate that a seris of Probe1,2&3-L1-D1-FETL-D2 conjugates can also be employed in this method.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

Example 1

2,3,4,5-Tetrachloro-6-(2-(4'-carboxyphenyl)-7-chloro-6-hydroxy-3-oxo-3H-xanthen-9-yl)-benzoic acid

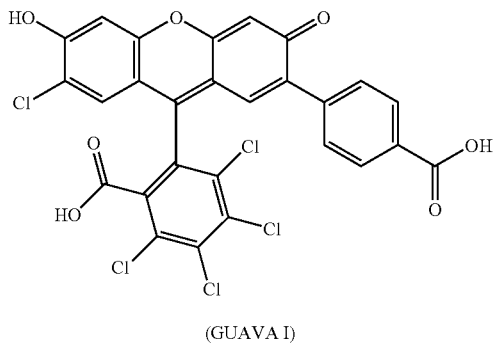

(GUAVA I)

1A. 2,3,4,5-Tetrachloro-6-(5-chloro-2,4-dihydroxy-benzoyl)-benzoic acid (0.43 g, 1.0 mmol) and 2',4'-dihydroxy-biphenyl-4-carboxylic acid (3, 0.23 g, 1.0 mmol) in methanesulfonic acid (10 mL) was placed in a pre-heated oil bath (T=130° C.) and stirred over a period of 2 h. The reaction mixture was allowed to cool to room temperature and quenched by pouring into ice cold water (200 mL). The solution was allowed to stand over a period of 2 h and the crude product was extracted with ethylacetate (EtOAc, 2×100 mL). The combined organic portions were washed with water (1×100 mL), and saturated sodium chloride (1×100 mL), dried ($Na_2SO_4$), and concentrated to give crude 1 as a dark brown solid. Purification via column chromatography (silica gel, 100 g, 1/1 EtOAc:hexanes 0.5% AcOH) gave the title compound (0.26 g, 42%) as an orange solid. Absorbance maximum ($\lambda_{max}$ 540 nm, 1×PBS), emission maximum ($\lambda_{em}$ 570 nm, 1×PBS).

1B. By following the procedure of Example 1A and substituting 2,3,4,5-tetrachloro-6-(5-chloro-2,4-dihydroxy-benzoyl)-benzoic acid with the following:

2,3,4,5-tetrabromo-6-(5-chloro-2,4-dihydroxy-benzoyl)-benzoic acid; and 4-carboxy-2,3,5-trichloro-6-(5-chloro-2,4-dihydroxy-benzoyl)-benzoic acid, there are obtained the following respective compounds of Formula D1:

2,3,4,5-tetrabromo-6-(2-(4'-carboxyphenyl)-7-chloro-6-hydroxy-3-oxo-3H-xanthen-9-yl)-benzoic acid; and 4-carboxy-2,3,5-trichloro-6-(2-(4'-carboxyphenyl)-7-chloro-6-hydroxy-3-oxo-3H-xanthen-9-yl)-benzoic acid.

Example 2

2,3,4,5-Tetrachloro-6-(2,7-bis(4'-carboxyphenyl)-6-hydroxy-3-oxo-3H-xanthen-9-yl)-benzoic acid)

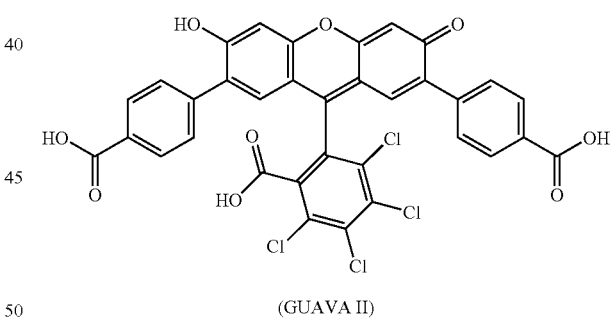

(GUAVA II)

Tetrachloropthallic anhydride (31 mg, 0.11 mmol) and 2',4'-dihydroxy-biphenyl-4-carboxylic acid (50 mg, 0.22 mmol) in methanesulfonic acid (2 mL) was placed in an pre-heated oil bath (T=130° C.) and stirred over a period of 0.75 h. The reaction mixture was allowed to cool to room temperature and quenched by pouring into ice cold water (50 mL). The solution was allowed to stand over a period of 2 h and the crude product was extracted with ethylacetate (EtOAc, 3×25 mL). The combined organic portions were washed with water (1×50 mL), and saturated sodium chloride (1×50 mL), dried ($Na_2SO_4$), and concentrated to give crude 1 as a dark brown solid. Purification via preparative layer chromatography (silica gel RP-18, 1 mm, 95/35 100 mM TEAB: AcCN, ×2) giving 4 as the major product. $\lambda_{max}$ 550 nm, MeOH; $\lambda_{em}$ 575 nm, MeOH.

Example 3

2,3,4,5-Tetrachloro-6-(4-(4'-carboxyphenyl)-5-hydroxy-9-oxo-9H-benzo[a]xanthen-12-yl)-benzoic acid

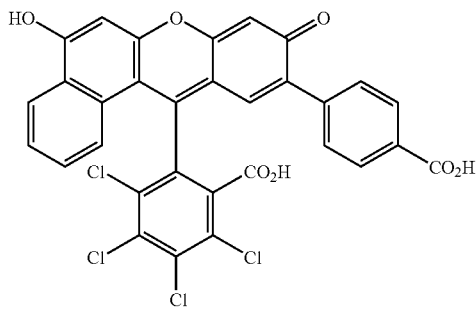

(GUAVA III)

Tetrachloropthallic anhydride (0.32 g, 1.1 mmol) and 2',4'-dihydroxy-biphenyl-4-carboxylic acid (0.26 g, 1.1 mmol), 1,3-dihydroxynaphtalene (0.18 g, 1.1 mmol), in methanesulfonic acid (4 mL) was placed in an pre-heated oil bath (T=110° C.) and stirred over a period of 17 h. The reaction mixture was allowed to cool to room temperature and quenched by pouring into ice cold water (100 mL). The solution was allowed to stand over a period of 2 h and the crude product was extracted with ethylacetate (EtOAc, 3×25 mL). The combined organic portions were washed with water (1×50 mL), and saturated sodium chloride (1×50 mL), dried (Na$_2$SO$_4$), and concentrated to give crude 1 as a dark brown solid. Purification via column chromatography (silica gel 50 g, 4/1 EtOAc:hexanes, 1% AcOH) giving the title compound as the major product. ABS $\lambda_{max}$ 540 nm, 1×PBS; EM $\lambda_{em}$ 570 nm, 1×PBS.

Example 4

2,3,4,5-Tetrachloro-6-(4-(6'-carboxynaphtyl)-5-hydroxy-9-oxo-9H-benzo[a]xanthen-12-yl)-benzoic acid

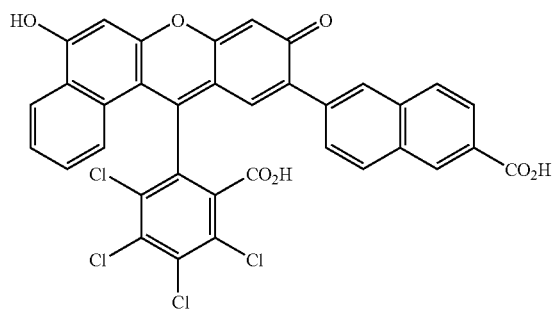

(GUAVA IV)

Tetrachloropthallic anhydride (0.32 g, 1.1 mmol) and 6-(2',4'-dihydroxyphenyl-2-naphthoic acid (0.31 g, 1.1 mmol), 1,3-dihydroxynaphthalene (0.18 g, 1.1 mmol), in methanesulfonic acid (5 mL) was placed in an pre-heated oil bath (T=110° C.) and stirred over a period of 17 h. The reaction mixture was allowed to cool to room temperature and quenched by pouring into ice cold water (100 mL). The solution was allowed to stand over a period of 2 h and the crude product was extracted with ethylacetate (EtOAc, 2×100 mL). The combined organic portions were washed with water (1×100 mL), and saturated sodium chloride (1×100 mL), dried (Na$_2$SO$_4$), and concentrated to give crude 6 as a dark brown solid. Purification via column chromatography (silica gel 50 g, 4/1 EtOAc:hexanes, 1% AcOH) giving the title compound as the major product. ABS $\lambda_{max}$ 541 nm, 1×PBS; EM $\lambda_{em}$ 574 nm, 1×PBS.

Example 5

2,3,4,5-Tetrachloro-6-(2-(6'-carboxynaphthyl)-7-chloro-6-hydroxy-3-oxo-3H-xanthen-9-yl)-benzoic acid

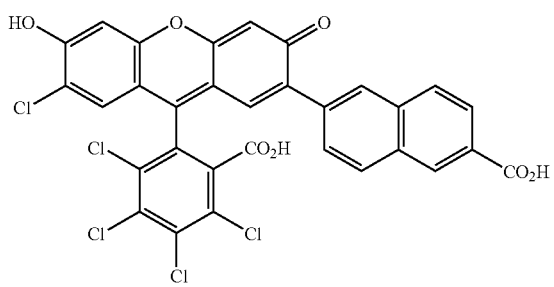

(GUAVA VII)

2,3,4,5-Tetrachloro-6-(5-chloro-2,4-dihydroxy-benzoyl)-benzoic acid (0.43 g, 1.0 mmol) and 6-(2',4'-dihydroxyphenyl)-2-naphthoic acid (0.28 g, 1.0 mmol) in methanesulfonic acid (10 mL) are placed in a pre-heated oil bath (T=130° C.) and stirred over a period of 2 h. The reaction mixture is allowed to cool to room temperature and quenched by pouring into ice cold water (200 mL). The solution is allowed to stand over a period of 2 h and the crude product is extracted with ethylacetate (EtOAc, 2×100 mL). The combined organic portions are washed with water (1×100 mL), and saturated sodium chloride (1×100 mL), dried (Na$_2$SO$_4$), and concentrated to give crude 7 as a dark brown solid. Purification via column chromatography (silica gel, 100 g, 1/1 EtOAc:hexanes 0.5% AcOH) gives the title compound 7. Expected yield (0.26 g, 42%). Expected absorbance maximum ($\lambda_{max}$ 550 nm, MeOH), expected emission maximum ($\lambda_{em}$ 576 nm, MeOH).

Example 6

2,3,4,5-Tetrachloro-6-{2-(4'-carboxyphenyl)-7-chloro-6-hydroxy-3-oxo-4-[(2,2,2-trifluoro-acetylamino)methyl]-3H-xanthen-9-yl}-benzoic acid, and 2,3,4,5-Tetrachloro-6-{2-(4'-carboxyphenyl)-7-chloro-6-hydroxy-3-oxo-5-[(2,2,2-trifluoro-acetylamino)methyl]-3H-xanthen-9-yl}-benzoic acid

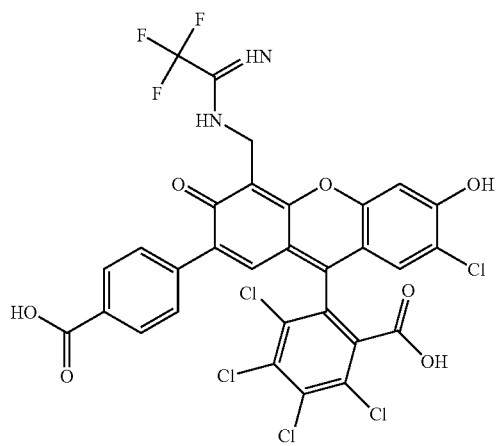

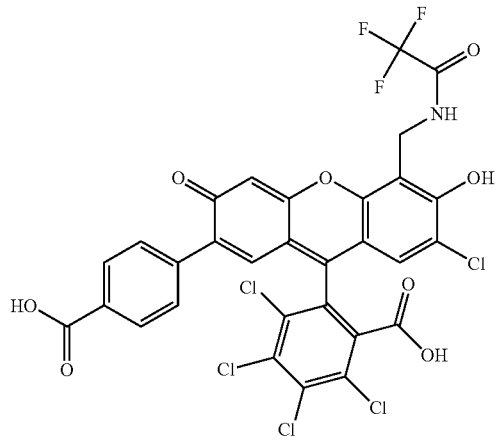

4- or 5-trifluoroacetylaminomethyl Guava I (GI-AMTFA)

A solution of 2,3,4,5-tetrachloro-6-(2-(4'-carboxyphenyl)-7-chloro-6-hydroxy-3-oxo-3H-xanthen-9-yl)-benzoic acid (200 mg, 0.32 mmol, as prepared in Example 1), and N-(hydroxymethyl) trifluoroacetamide (44 mg, 0.31 mmol, Lancaster, Inc) in sulfuric acid (3 mL) was stirred at room temperature over a period of 16 h then poured into crushed ice (25 g). The crude product was extracted with EtOAc (2×50 mL) and the combined organic portions were washed with water (1×50 mL) and saturated NaCl (1×50 mL), dried (MgSO$_4$) and concentrated. Purification via column chromatography (silica gel, 60 g, 1/1 EtOAc/hexanes 1% AcOH) gave the title compounds as a mixture (105 mg, 62%).

Example 7

2-{7-[4-(5-carboxy-pentylcarbamoyl)-phenyl]-2-chloro-6-hydroxy-3-oxo-3H-xanthen-9-yl}-3,4,5,6-tetrachloro-benzoic acid anion

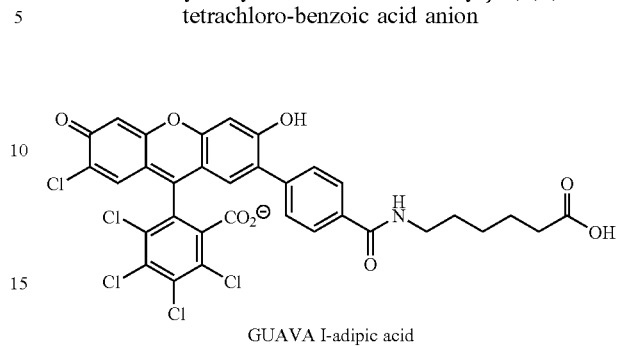

GUAVA I-adipic acid

To a stirring solution of 2,3,4,5-tetrachloro-6-(2-(4'-carboxyphenyl)-7-chloro-6-hydroxy-3-oxo-3H-xanthen-9-yl)-benzoic acid (50 mg, 0.08 mmol, as prepared in Example 1), 6-aminohexanoic acid (10 mg, 0.084 mmol) in N,N-dimethylformamide (DMF, 1 mL) was added dicyclohexylcarbodiimide (DCC, 17 mg, 0.084 mmol) and 1-hydroxybenzotriazole (HOBT, 10 mg, 0.08 mmol). The reaction mixture was allowed to stir at room temperature under nitrogen gas over a period of 16 h followed by addition of a 1/1 EtOAc:water (100 mL). The organic portion was washed with water (2×20 mL), HCl (2M, 1×20 mL) and saturated sodium chloride (1×20 mL), dried (Na$_2$SO$_4$) and concentrated. Purification via preparative layer chromatography (PLC, silica gel, 1 mm, 5/1 EtOAc/hexanes 1% AcOH) gave the title compound (40 mg, 67%). ABS $\lambda_{max}$ 529 nm, 1×PBS pH 7.4.

Example 8

2,3,4,5-Tetrachloro-6-{2-(4'-carboxyphenyl)-7-chloro-6-hydroxy-4-[(5-methoxycarbonyl-pentanoylamino)methyl]-3-oxo-3H-xanthen-9-yl}-benzoic acid

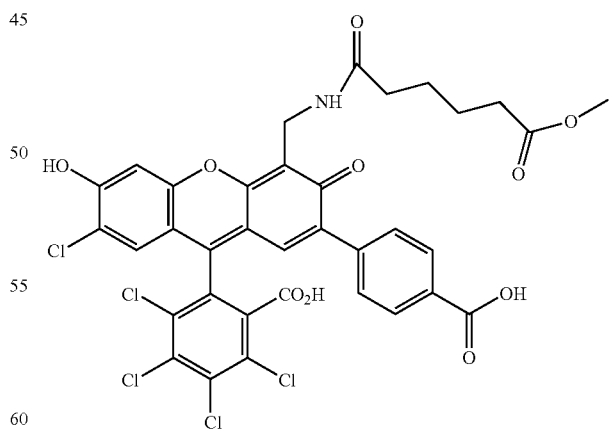

L1-Amino-methyl GUAVA I 2,3,4,5-Tetrachloro-6-{22-(4'-carboxyphenyl)-7-chloro-6-hydroxy-3-oxo-4-[(2,2,2-trifluoro-acetylamino)-methyl]-3H-xanthen-9-yl}-benzoic acid (3 mg, 4 μmol) was deprotected with concentrated ammonium hydroxide at 50° C.

over a period over 0.5 h and concentrated to dryness. The resulting free amine was reacted with hexanedioic acid-1-succinimidyl ester-6-methyl ester (1 eq.) in a solution of DMF:diisopropylethylamine (DIEA), 100/15, 1.15 ml. After a period of 1 h the reaction mixture was concentrated and purified by preparative layer chromatography (silica gel, 1 mm, 95/5 DCM: MeOH, 0.5% AcOH) to give the title compound (2 mg, 62%).

Example 9

1-(4-Methoxycarbonyl-benzyl)-2-{5-[1-(4-methoxy-carbonyl-benzyl)-3,3-dimethyl-5-sulfo-1,3-dihydro-indol-2-ylidene]-penta-1,3-dienyl}-3,3-dimethyl-5-sulfo-3H-indolium

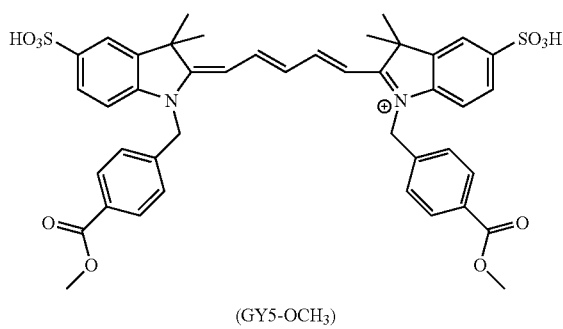

(GY5-OCH₃)

A stirring solution of 1-(4-methoxycarbonyl-benzyl)-2,3,3-trimethyl-5-sulfo-3H-indolium (0.2 g, 0.4 mmol), tetramethoxypropane (33 µL, 0.2 mmol), acetic anhydride (230 µL, 2.4 mmol), acetic acid (23 µL, 0.4 mmol) and N-methylpyrrolidone was heated to 50° C. over a period of 16 h. The reaction mixture was cooled to room temperature followed by addition of water (10 mL). The aqueous portion was washed with EtOAc (2×30 mL) to remove organic impurities and concentrated. The dark blue concentrate was purified via preparative layer chromatography (PLC, 1 mm RP-C18, 25% acetonitrile:water to give the title compound. ABS $\lambda_{max}$ 648, EM $\lambda_{em}$ 670 1×PBS.

Example 10

1-(4-Carboxy-benzyl)-2-{5-[1-(4-carboxy-benzyl)-3,3-dimethyl-5-sulfo-1,3-dihydro-indol-2-ylidene]-penta-1,3-dienyl}-3,3-dimethyl-5-sulfo-3H-indolium

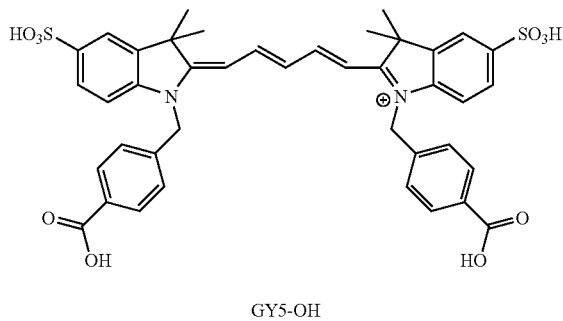

GY5-OH

Purified 1-(4-Methoxycarbonyl-benzyl)-2-{5-[1-(4-methoxycarbonyl-benzyl)-3,3-dimethyl-5-sulfo-1,3-dihydro-indol-2-ylidene]-penta-1,3-dienyl}-3,3-dimethyl-5-sulfo-3H-indolium (3 mg, 3.4 µmol) was dissolved in potassium hydroxide (KOH, 8 M, 340 µL) and water (60 µL) and heated to 50° C. over a period of 1 h. The reaction mixture was neutralized with concentrated HCl (28 µL) and the precipitated title product was collected by filtration. ABS $\lambda_{max}$ 648 nm, 1×PBS.

Example 11

(4-Carboxy-benzyl)-[10-(4-carboxy-phenyl)-7-dimethylamino-9,9-dimethyl-9H-anthracen-2-ylidene]-ethyl-ammonium

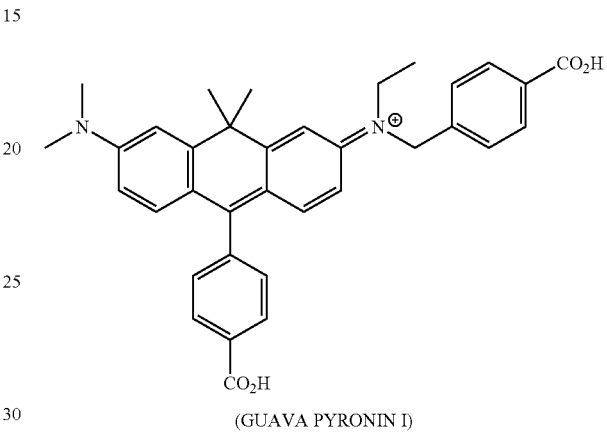

(GUAVA PYRONIN I)

To an ice cold solution of 4-{[(4-hydroxymethyl-phenyl)-methyl-amino]-methyl}-benzoic acid methyl ester (0.5 g, 1.8 mmol) and 3-isopropenyl-phenyl)-dimethyl-amine (0.31 g, 1.9 mmol) in methylene chloride (CH₂Cl₂, 25 mL)) is added dropwise a solution of boron trichloride (1 M BCl₃ in CH₂Cl₂, 2 mL). The reaction mixture is allowed to stir overnight at room temperature cooled to −15° C. (NaCl/water) followed by dropwise addition of concentrated sulfuric acid (12 mL). Methylene chloride is removed and the mixture is allowed to stand at 40° C. over a period of 16 h. The resulting solution is poured into crushed ice and neutralized with 2 N sodium hydroxide. The aqueous solution is extracted with methylene chloride (2×75 ml), dried (Na₂SO₄) and concentrated giving the 9,10-dihydro-anthracene as a residue.

The residue is taken up in ethanol (100 mL) followed by addition of perchloric acid (60%, 1 ml) and tetrabutylammonium(meta)periodate (0.078 g, 0.18 mmol) and the solution is refluxed over a period of 0.5 h. The reaction mixture is cooloed to room temperature and poured into a solution of sodium perchlorate (0.2 M, NaClO₄, 200 ml) and allowed to stand overnight. The solid precipitate is collected by filtration and dried to give the corresponding 2,9-dihydro-anthracene product. Expected yield (0.4–0.5 g, 40–50%).

To a −78° C. stirring solution of 2-(4-bromophenyl)-4,4-dimethyl-2-oxazole (10 eq) and t-butyllithium in THF (10 ml) is added the 2,9-dihydro-anthracene (0.1 g, 0.23 mmol) in anhydrous tetrahydrofuran (THF, 2 ml) dropwise. The reaction mixture allowed to stir at −50–60° C. until the reaction is complete (TLC). The reaction is quenched by addition of saturated ammonium chloride (10 mL) and the product extracted with methylene chloride. Purification via column chromatography (silica gel, 40 g, 90/10 methylene chloride:MeOH) gives the oxazole protected Guava pyronin 1-oxazole (GPO).

The oxazole protecting group is converted to the carboxylic acid by treatment of GPO with 3M HCl in ethanol to give the title compound Guava pyronin1.

Example 12

8-(6-Ethylamino-3-ethylimino-2,7-dimethyl-3H-xanthen-9-yl)naphthalene-1-carboxylic acid

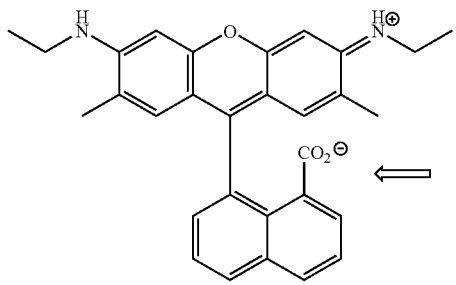

3-Ethylamino-4-methyl-phenol (0.3 g, 2 mmol) and benzo[de]isochromene-1,3-dione (0.2 g, 1 mmol) in sulfuric acid (3 ml) was heated to 150° C. over a period of 6 h. The reaction mixture was pouring into crushed ice, allowed to stand over a period of 1 h and the precipitate was filtered. The filtrate was neutralized with concentrated ammonium hydroxide and concentrated to give a dark purple residue. Purification via preparatory layer chromatography (PLC, 1 mm silica gel, 9/1 DCM: MeOH, 2% AcOH) gave the title compound (50 mg). ABS $\lambda_{max}$=527 nm (EtOH).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

We claim:
1. A fluorescence energy transfer dye having the Formula I:

-L1-D1-FETL-D2-L2- (Formula I)

where:
L1 is a link that is a chemical bond for attachment to a probe or target, for attachment to a solid support, or is absent;
L2 is a link that is a chemical bond for attachment to a probe or target, for attachment to a solid support, or is absent;
FETL is a fluorescence energy transfer linker that is a symmetric, rigid or sterically hindered, divalent moiety joined to D1 and D2 via an amine, carbonyl, activated carboxylic acid ester, disulfide, thiol or thiol ester;

D1 is a donor dye represented by the formula:

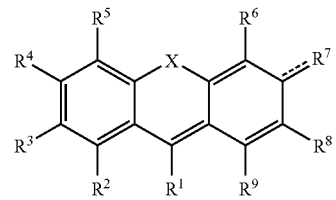

where:
X is O or C(R*R**), where R* and R** are independently lower alkyl or —CH$_2$-Z;
$R^1$ is H, CF$_3$, perfluoropropyl, lower alkyl acid, substituted aryl, substituted heteroaryl or Z;
$R^2$ is H, halo, SO$_3^-$, or is taken together with $R^3$ to form an optionally substituted fused ring having 5 to 7 atoms;
$R^3$ is halo, Z, or is taken together with $R^2$ and/or $R^4$ to form an optionally substituted fused ring having 5 to 7 atoms;
$R^4$ is =O or OH, —N(R$^{4'}$R$^{4''}$) or =N$^+$(R$^{4'}$R$^{4''}$), or is taken together with $R^3$ and/or $R^5$ to form an optionally substituted fused ring having 5 to 7 atoms,
where R$^{4'}$ is H, lower alkyl or L1, and
R$^{4''}$ is H, lower alkyl or CH$_2$-Z;
$R^5$ is H, halo, Z, or is taken together with $R^4$ to form an optionally substituted fused ring having 5 to 7 atoms;
$R^6$ is H, halo, Z, or is taken together with $R^7$ to form an optionally substituted fused ring having 5 to 7 atoms;
$R^7$ is =O or OH, —N(R$^{7'}$R$^{7''}$) or =N$^+$(R$^{7'}$R$^{7''}$), or is taken together with $R^6$ and/or $R^8$ to form an optionally substituted fused ring having 5 to 7 atoms,
where R$^{7'}$ is H, lower alkyl or L1, and
R$^{7''}$ is H, lower alkyl or CH$_2$-Z;
$R^8$ is halo, Z, or is taken together with $R^7$ and/or $R^9$ to form an optionally substituted fused ring having 5 to 7 atoms;
$R^9$ is H, halo, SO$_3^-$, or is taken together with $R^8$ to form an optionally substituted fused ring having 5 to 7 atoms; and
Z is a group of the formula: -Z*-Z$^1$-(linkage to L1, L2 or FETL), where:
Z* is methylene, methoxy, ethoxy, aminomethyl, aminoethyl, aminopropynyl, aminobutynyl, carboxyethenyl, carboxyethynyl, optionally substituted aryl or optionally substituted heteroaryl;
Z$^1$ is —C(O)—, —N(Z$^2$)-, —CH$_2$—O—, —CH$_2$—C(O)—, —CH$_2$—N(Z$^2$)-, —CH$_2$—S—, —CH$_2$—S(O)—, —CH$_2$—S(O$_2$)— or is absent; and
Z$^2$ is H, C$_1$ to C$_8$ optionally substituted lower alkyl, or optionally substituted aryl; and
D2 is an acceptor/reporter dye represented by formula D1 or by a formula of the group:

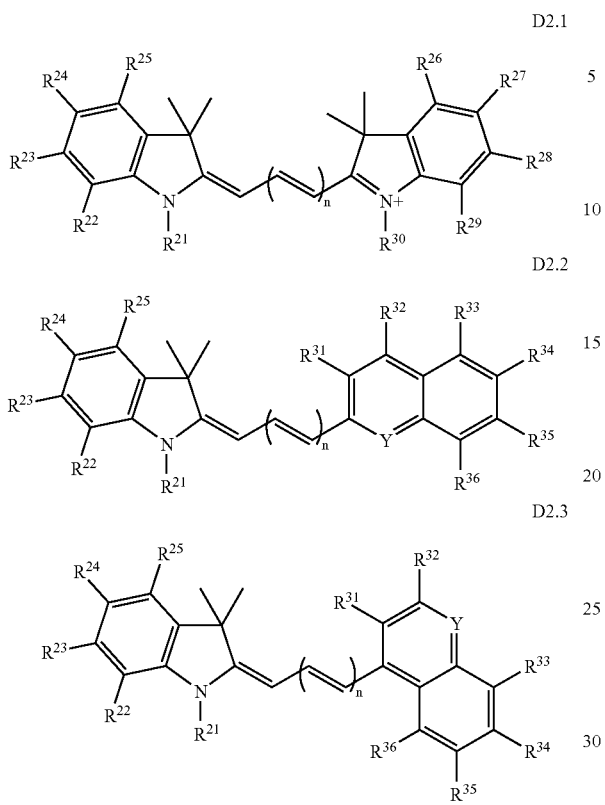

where:
at least one of $R^{21}$ to $R^{36}$ is joined to FETL,
n is zero, 1, 2 or 3;
$R^{21}$ and $R^{30}$ are independently —CH$_2$-Z, activated lower alkyl, or optionally substituted aralkyl;
$R^{22}$ to $R^{29}$ are independently H, SO$_3^-$, or optionally substituted alkyl, or $R^{22}$ and $R^{23}$, $R^{23}$ and $R^{24}$, $R^{24}$ and $R^{25}$, $R^{26}$ and $R^{27}$, $R^{27}$ and $R^{28}$, and/or $R^{28}$ and $R^{29}$ taken together form an optionally substituted fused ring having 6 atoms;
$R^{31}$ and $R^{32}$ are independently H, optionally substituted alkyl, aryl, or taken together form an optionally substituted fused ring having 6 atoms;
$R^{33}$ to $R^{36}$ are independently H, SO$_3^-$, optionally substituted alkyl, aryl, or $R^{33}$ and $R^{34}$, $R^{34}$ and $R^{35}$, and/or $R^{35}$ and $R^{36}$ taken together form an optionally substituted fused ring having 6 atoms; and
Y is —O— or —N(Y$^1$)— where Y$^1$ is —CH$_2$-Z, activated lower alkyl, or optionally substituted aralkyl;
provided that at least one of $R^3$ to $R^8$ is Z where Z* is optionally substituted aryl or optionally substituted heteroaryl.

2. The fluorescence energy transfer dye of claim 1 having one or more of the following:
$R^1$ is H, CF$_3$, perfluoropropyl, lower alkyl acid, 5–6 membered mono or 10–12 membered fused substituted aryl or heteroaryl, or Z;
$R^2$ is H, halo, SO$_3^-$, or is taken together with $R^3$ to form an optionally substituted fused 6-membered aryl ring;
$R^3$ is halo, Z, or is taken together with $R^2$ and/or $R^4$ to form an optionally substituted fused 6-membered ring;
$R^4$ is =O or OH, —N(R$^4$'R$^{4"}$) or =N$^+$(R$^4$'R$^{4"}$), or is taken together with $R^3$ and/or $R^5$ to form an optionally substituted fused 6-membered ring;
$R^5$ is H, halo, Z, or is taken together with $R^4$ to form an optionally substituted fused 6-membered ring;
$R^6$ is H, halo, Z, or is taken together with $R^7$ to form an optionally substituted fused 6-membered ring;
$R^7$ is =O or OH, —N(R$^7$'R$^{7"}$) or =N$^+$(R$^7$'R$^{7"}$), or is taken together with $R^6$ and/or $R^8$ to form an optionally substituted fused 6-membered ring;
$R^8$ is halo, Z, or is taken together with $R^7$ and/or $R^9$ to form an optionally substituted fused 6-membered ring;
$R^9$ is H, halo, SO$_3^-$, or is taken together with $R^8$ to form an optionally substituted fused 6-membered aryl ring;
$R^4$ is —N(R$^4$'R$^{4"}$) or =N$^+$(R$^4$'R$^{4"}$) and $R^7$ is —N(R$^7$'R$^{7"}$) or =N$^+$(R$^7$'R$^{7"}$) when X is C(R*R**);
Z is a group of the formula: -Z*-Z$^1$-(L1, L2 or FETL), where:
Z* is methylene, methoxy, ethoxy, aminomethyl, aminoethyl, aminopropynyl, aminobutynyl, carboxyethenyl, carboxyethynyl, optionally substituted aryl or optionally substituted heteroaryl,
Z$^1$ is —C(O)—, —N(Z$^2$)-, —CH$_2$—O—, —CH$_2$—C(O)—, —CH$_2$—N(Z$^2$)-, —CH$_2$—S—, —CH$_2$—S(O)—, —CH$_2$—S(O$_2$)— or is absent, and
Z$^2$ is H, or is C$_1$ to C$_8$ lower alkyl or aryl optionally substituted with SO$_3^-$, COOH, NH$_2$, CH$_2$NH$_2$, SH, or SCH$_3$;
$R^{21}$ or $R^{30}$ is carboxy-naphthyl-methyl, mono- or di-ortho-substituted benzyl having an ortho-, meta- or para-carbonyl or activating group, or an activated C$_1$ to C$_6$ lower alkyl;
$R^{22}$ to $R^{29}$ are independently H, SO$_3^-$ or optionally substituted alkyl, or $R^{22}$ and $R^{23}$, $R^{23}$ and $R^{24}$, $R^{24}$ and $R^{25}$, $R^{26}$ and $R^{27}$, $R^{27}$ and $R^{28}$, and/or $R^{28}$ and $R^{29}$ taken together form a fused, sulfonated 6-membered aryl ring;
$R^{31}$ and $R^{32}$ are independently H, optionally substituted alkyl, aryl, or taken together form a fused, sulfonated 6-membered carbocyclic or heterocyclic ring;
$R^{33}$ to $R^{36}$ are independently H, SO$_3^-$, optionally substituted alkyl, aryl, or $R^{33}$ and $R^{34}$, $R^{34}$ and $R^{35}$, and/or $R^{35}$ and $R^{36}$ taken together form a fused, sulfonated 6-membered carbocyclic or heterocyclic ring; and/or
at least one of $R^{22}$ to $R^{29}$ or $R^{33}$ to $R^{36}$ is SO$_3^-$.

3. The fluorescence energy transfer dye of claim 2 having one or more of the following:
$R^1$ is H, CF$_3$, perfluoropropyl, lower alkyl acid, an optionally substituted ortho-benzoic acid, or Z;
$R^2$ is H, halo or SO$_3^-$;
$R^3$ is halo or Z;
$R^4$ is =O or OH, —N(R$^4$'R$^{4"}$) or =N$^+$(R$^4$'R$^{4"}$);
$R^5$ is H, halo or Z;
$R^6$ is H, halo or Z;
$R^7$ is =O or OH, —N(R$^7$'R$^{7"}$) or =N$^+$(R$^7$'R$^{7"}$);
$R^8$ is Z;
$R^9$ is H, halo or SO$_3^-$;
Z is a group of the formula: -Z*-Z$^1$-(L1, L2 or FETL), where:
Z* is an optionally substituted aryl or heteroaryl of the group: phenyl, adamantyl, norboranyl, biphenyl, naphthyl, furanyl, bifuranyl, thiophenyl, bithienyl, pyrrolyl, indolyl, isoindolyl, benzofuranyl, isobenzofuranyl, benzothiophenyl, benzothienyl, chromenyl and isochromenyl, and
Z$^1$ is —C(O)—, —N(H)—, —CH$_2$—O—, —CH$_2$—C(O)—, —CH$_2$—N(H)—, or is absent;

$R^{22}$ to $R^{29}$ are independently H, $SO_3^-$ or optionally substituted alkyl, or $R^{24}$ and $R^{25}$ and/or $R^{26}$ and $R^{27}$ taken together form a fused, sulfonated 6-membered aryl ring;

$R^{31}$ and $R^{32}$ are independently H, optionally substituted alkyl or aryl; and/or $R^{33}$ to $R^{36}$ are independently H, $SO_3^-$, optionally substituted alkyl or aryl.

4. The fluorescence energy transfer dye of claim 3 where $R^1$ is a group represented by Formula R1.1:

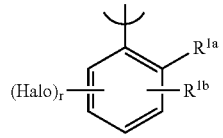

where:
$R^{1a}$ is H, halo or —C(O)O$^-$;
$R^{1b}$ is H, halo or —C(O)-(L1, L2 or FETL);
$R^{1c}$ is halo; and
r is 0, 1, 2 or 3.

5. The fluorescence energy transfer dye of claim 1 where at least one of $R^3$ to $R^8$ is Z where Z* is optionally substituted aryl selected from phenyl, adamantyl, norboranyl, biphenyl and naphthyl.

6. The fluorescence energy transfer dye of claim 5 where Z* is phenyl and $Z^1$ is —C(O)—.

7. The fluorescence energy transfer dye of claim 1 where:
$R^1$ is H, $CF_3$, perfluoropropyl, lower alkyl acid, an optionally substituted ortho-benzoic acid, or Z;
$R^2$ is H, halo or $SO_3^-$;
$R^3$ is halo or Z;
$R^4$ is =O or OH, —N($R^{4'}R^{4''}$) or =N$^+$($R^{4'}R^{4''}$);
$R^5$ is H, halo or Z;
$R^6$ is H, halo or Z;
$R^7$ is =O or OH, —N($R^{7'}R^{7''}$) or =N$^+$($R^{7'}R^{7''}$);
$R^8$ is Z;
$R^9$ is H, halo or $SO_3^-$;
Z is a group of the formula: -Z*-$Z^1$-(L1, L2 or FETL), where:
Z* is an optionally substituted aryl or heteroaryl of the group: phenyl, adamantyl, norboranyl, biphenyl, naphthyl, furanyl, bifuranyl, thiophenyl, bithienyl, pyrrolyl, indolyl, isoindolyl, benzofuranyl, isobenzofuranyl, benzothiophenyl, benzothienyl, chromenyl and isochromenyl, and
$Z^1$ is —C(O)—, —N(H)—, —CH$_2$—O—, —CH$_2$—C(O)—, —CH$_2$—N(H)—, or is absent;
$R^{21}$ or $R^{30}$ is carboxy-naphthyl-methyl, mono- or di-ortho-substituted benzyl having an ortho-, meta- or para-carbonyl or activating group, or an activated $C_1$ to $C_6$ lower alkyl;
$R^{22}$ to $R^{29}$ are independently H, $SO_3^-$ or optionally substituted alkyl, or $R^{24}$ and $R^{25}$ and/or $R^{26}$ and $R^{27}$ taken together form a fused, sulfonated 6-membered aryl ring;
$R^{31}$ and $R^{32}$ are independently H, optionally substituted alkyl or aryl; and
$R^{33}$ to $R^{36}$ are independently H, $SO_3^-$, optionally substituted alkyl or aryl.

8. The fluorescence energy transfer dye of claim 1 where FETL is represented by a formula of the group:

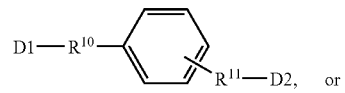

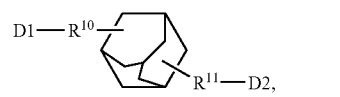

where:
$R^{10}$ is —C(O)—, —N(H)—CH$_2$—, —S—C(O)—, —O—C(S)— or —S—CH$_2$—; and
$R^{11}$ is —C(O)—, —CH$_2$—N(H)—; —C(O)—S—, —C(S)—O— or CH$_2$—S—;

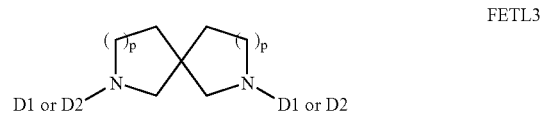

where:
p is independently 0, 1, 2 or 3; and

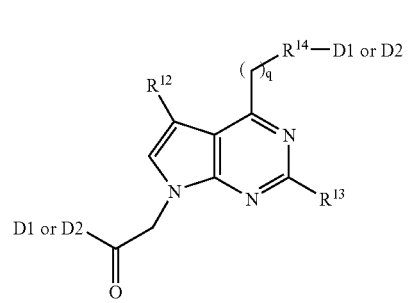

where:
q is zero or 1;
$R^{12}$ is H, halo, or optionally substituted-alkyl, -alkenyl, -alkynyl or -aryl;
$R^{13}$ is H, $SO_3^-$ or optionally substituted-alkyl, -alkenyl, -alkynyl or -aryl; and
$R^{14}$ is a secondary or tertiary amine or heterocyclyl, particularly N(H) or piperazine.

9. The fluorescence energy transfer dye of claim 8 where FETL is FETL1 and:
$R^{10}$ is —C(O)— or —N(H)—CH$_2$—; and
$R^{11}$ is —C(O)— or —CH$_2$—N(H)—.

10. An compound represented by the formula:

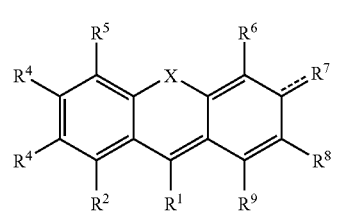

where:
- X is O or C(R*R**), where R* and R** are independently lower alkyl or —CH$_2$-Z;
- R$^1$ is H, CF$_3$, perfluoropropyl, lower alkyl acid, substituted aryl, substituted heteroaryl or Z;
- R$^2$ is H, halo, SO$_3^-$, or is taken together with R$^3$ to form an optionally substituted fused ring having 5 to 7 atoms;
- R$^3$ is halo, Z, or is taken together with R$^2$ and/or R$^4$ to form an optionally substituted fused ring having 5 to 7 atoms;
- R$^4$ is =O or OH, —N(R$^{4'}$R$^{4''}$) or =N$^+$(R$^{4'}$R$^{4''}$), or is taken together with R$^3$ and/or R$^5$ to form an optionally substituted fused ring having 5 to 7 atoms, where R$^{4'}$ is H, lower alkyl or L1, and R$^{4''}$ is H, lower alkyl or CH$_2$-Z;
- R$^5$ is H, halo, Z, or is taken together with R$^4$ to form an optionally substituted fused ring having 5 to 7 atoms;
- R$^6$ is H, halo, Z, or is taken together with R$^7$ to form an optionally substituted fused ring having 5 to 7 atoms;
- R$^7$ is =O or OH, —N(R$^{7'}$R$^{7''}$) or =N$^+$(R$^{7'}$R$^{7''}$), or is taken together with R$^6$ and/or R$^8$ to form an optionally substituted fused ring having 5 to 7 atoms, where R$^{7'}$ is H, lower alkyl or L1, and R$^{7''}$ is H, lower alkyl or CH$_2$-Z;
- R$^8$ is halo, Z, or is taken together with R$^7$ and/or R$^9$ to form an optionally substituted fused ring having 5 to 7 atoms;
- R$^9$ is H, halo, SO$_3^-$, or is taken together with R$^8$ to form an optionally substituted fused ring having 5 to 7 atoms; and
- Z is a group of the formula: -Z*-Z$^1$-(L1, L2 or FETL), where:
  - Z* is methylene, methoxy, ethoxy, aminomethyl, aminoethyl, aminopropynyl, aminobutynyl, carboxyethenyl, carboxyethynyl, optionally substituted aryl or optionally substituted heteroaryl;
  - Z$^1$ is —C(O)—, —N(Z$^2$)-, —CH$_2$—O—, —CH$_2$—C(O)—, —CH$_2$—N-(Z$^2$)-, —CH$_2$—S—, —CH$_2$—S(O)—, —CH$_2$—S(O$_2$)— or is absent; and
  - Z$^2$ is H, C$_1$ to C$_8$ optionally substituted lower alkyl, or optionally substituted aryl;
- L1 being a link that is a chemical bond for attachment to a probe or target, for attachment to a solid support, or is absent;
- L2 being a link that is a chemical bond for attachment to a probe or target, for attachment to a solid support, or is absent; and
- FETL being a fluorescence energy transfer linker that is a symmetric, rigid or sterically hindered, divalent moiety joined to D1 and D2 via an amine, carbonyl, activated carboxylic acid ester, disulfide, thiol or thiol ester;

provided that at least one of R$^3$ to R$^8$ is Z, where Z* is optionally substituted aryl or optionally substituted heteroaryl.

11. The compound of claim 10 having one or more of the following:
- R$^1$ is H, CF$_3$, perfluoropropyl, lower alkyl acid, 5–6 membered mono or 10–12 membered fused substituted aryl or heteroaryl, or Z;
- R$^2$ is H, halo, SO$_3^-$, or is taken together with R$^3$ to form an optionally substituted fused 6-membered aryl ring;
- R$^3$ is halo, Z, or is taken together with R$^2$ and/or R$^4$ to form an optionally substituted fused 6-membered ring;
- R$^4$ is =O or OH, —N(R$^{4'}$R$^{4''}$) or =N$^+$(R$^{4'}$R$^{4''}$), or is taken together with R$^3$ and/or R$^5$ to form an optionally substituted fused 6-membered ring;
- R$^5$ is H, halo, Z, or is taken together with R$^4$ to form an optionally substituted fused 6-membered ring;
- R$^6$ is H, halo, Z, or is taken together with R$^7$ to form an optionally substituted fused 6-membered ring;
- R$^7$ is =O or OH, —N(R$^{7'}$R$^{7''}$) or =N$^+$(R$^{7'}$R$^{7''}$), or is taken together with R$^6$ and/or R$^8$ to form an optionally substituted fused 6-membered ring;
- R$^8$ is halo, Z, or is taken together with R$^7$ and/or R$^9$ to form an optionally substituted fused 6-membered ring;
- R$^9$ is H, halo, SO$_3^-$, or is taken together with R$^8$ to form an optionally substituted fused 6-membered aryl ring;
- R$^4$ is —N(R$^{4'}$R$^{4''}$) or =N$^+$(R$^{4'}$R$^{4''}$) and R$^7$ is —N(R$^{7'}$R$^{7''}$) or =N$^+$(R$^{7'}$R$^{7''}$) when X is C(R*R**); and/or
- Z is a group of the formula: -Z*-Z$^1$-(L1, L2 or FETL), where:
  - Z* is methylene, methoxy, ethoxy, aminomethyl, aminoethyl, aminopropynyl, aminobutynyl, carboxyethenyl, carboxyethynyl, optionally substituted aryl or optionally substituted heteroaryl,
  - Z$^1$ is —C(O)—, —N(Z$^2$)-, —CH$_2$—O—, —CH$_2$—C(O)—, —CH$_2$—N(Z$^2$)-, —CH$_2$—S—, —CH$_2$—S(O)—, —CH$_2$—S(O$_2$)— or is absent, and
  - Z$^2$ is H, or is C$_1$ to C$_8$ lower alkyl or aryl optionally substituted with SO$_3^-$, COOH, NH$_2$, CH$_2$NH$_2$, SH, or SCH$_3$.

12. A fluorescence energy transfer dye conjugate represented by Formula II:

Probe-L1-(D1 or D2)-FETL-(low affinity false target)     (Formula II)

where:
- Probe is a polynucleotide, antibody, triglyceride, low density lipoprotein or lectin;
- L1 is a link that is a chemical bond for attachment to a the Probe;
- FETL is a fluorescence energy transfer linker that is a symmetric, rigid or sterically hindered, divalent moiety joined to D1 and D2 via an amine, carbonyl, activated carboxylic acid ester, disulfide, thiol or thiol ester;
- low affinity false target is an analyte for the Probe disposed on FETL to deactivate, block or otherwise prevent coupling of FETL to a corresponding D2 or D1 until said low affinity false target is displaced by a higher affinity true target;
- D1 is a donor dye represented by the formula:

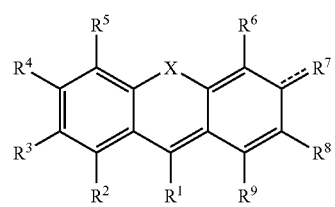

where:
- X is O or C(R*R**), where R* and R** are independently lower alkyl or —CH$_2$-Z;
- R$^1$ is H, CF$_3$, perfluoropropyl, lower alkyl acid, substituted aryl, substituted heteroaryl or Z;
- R$^2$ is H, halo, SO$_3^-$, or is taken together with R$^3$ to form an optionally substituted fused ring having 5 to 7 atoms;

R³ is halo, Z, or is taken together with R² and/or R⁴ to form an optionally substituted fused ring having 5 to 7 atoms;

R⁴ is =O or OH, —N(R⁴'R⁴") or =N⁺(R⁴'R⁴"), or is taken together with R³ and/or R⁵ to form an optionally substituted fused ring having 5 to 7 atoms,
where R⁴' is H, lower alkyl or L1, and
R⁴" is H, lower alkyl or CH₂-Z;

R⁵ is H, halo, Z, or is taken together with R⁴ to form an optionally substituted fused ring having 5 to 7 atoms;

R⁶ is H, halo, Z, or is taken together with R⁷ to form an optionally substituted fused ring having 5 to 7 atoms;

R⁷ is =O or OH, —N(R⁷' R⁷") or =N⁺(R⁷'R⁷"), or is taken together with R⁶ and/or R⁸ to form an optionally substituted fused ring having 5 to 7 atoms,
where R⁷' is H, lower alkyl or L1, and
R⁷" is H, lower alkyl or CH₂-Z;

R⁸ is halo, Z, or is taken together with R⁷ and/or R⁹ to form an optionally substituted fused ring having 5 to 7 atoms;

R⁹ is H, halo, SO₃⁻, or is taken together with R⁸ to form an optionally substituted fused ring having 5 to 7 atoms; and Z is a group of the formula: -Z*-Z¹-(L1, L2 or FETL), where:
Z* is methylene, methoxy, ethoxy, aminomethyl, aminoethyl, aminopropynyl, aminobutynyl, carboxyethenyl, carboxyethynyl, optionally substituted aryl or optionally substituted heteroaryl;
Z¹ is —C(O)—, —N(Z²)-, —CH₂—O—, —CH₂—C(O)—, —CH₂—N(Z²)-, —CH₂—S—, —CH₂—S(O)—, —CH₂—S(O₂)— or is absent; and
Z² is H, C₁ to C₈ optionally substituted lower alkyl, or optionally substituted aryl; and D2 is an acceptor/reporter dye represented by formula D1 or by a formula of the group:

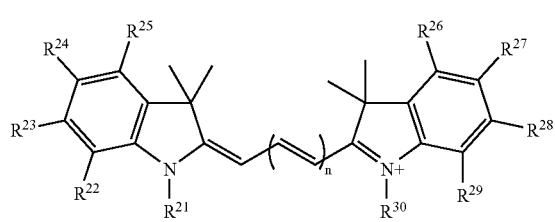

D2.1

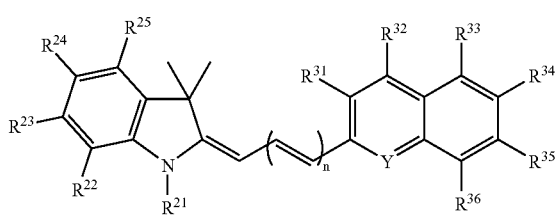

D2.2

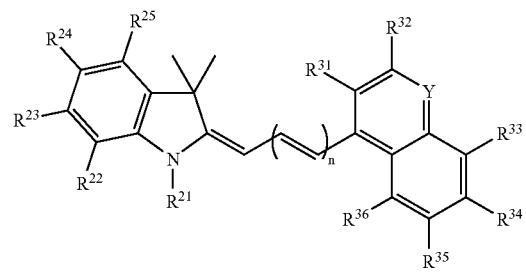

D2.3 where:
at least one of R²¹ to R³⁶ is joined to FETL,
n is zero, 1, 2 or 3;
R²¹ and R³⁰ are independently —CH₂-Z, activated lower alkyl, or optionally substituted aralkyl;
R²² to R²⁹ are independently H, SO₃⁻, or optionally substituted alkyl, or R²² and R²³, R²³ and R²⁴, R²⁴ and R²⁵, R²⁶ and R²⁷, R²⁷ and R²⁸, and/or R²⁸ and R²⁹ taken together form an optionally substituted fused ring having 6 atoms; and
R³¹ and R³² are independently H, optionally substituted alkyl, aryl, or taken together form an optionally substituted fused ring having 6 atoms;
R³³ to R³⁶ are independently H, SO₃⁻, optionally substituted alkyl, aryl, or R³³ and R³⁴, R³⁴ and R³⁵, and/or R³⁵ and R³⁶ taken together form an optionally substituted fused ring having 6 atoms; and
Y is —O— or —N(Y¹)— where Y¹ is —CH₂-Z, activated lower alkyl, or optionally substituted aralkyl.

13. A fluorescence energy transfer assay for determining the presence of a target site in a substance requiring no pre-analysis purification for removal of unbound dye, comprising the steps of:

(a) contacting a substance to be tested and a target site specific Probe-L1-(D1 or D2)-FETL-(low affinity false target) conjugate of claim 12 in a suitable assay vessel under conditions suitable for preferential binding of the Probe to the target site, as opposed to the low affinity false target;

(b) introducing into the vessel a D2 or D1 fluorescence energy transfer dye having an activated site for coupling to the FETL, under conditions suitable for coupling to FETL where the low affinity false target is not bound to the Probe, wherein the second dye is the other of the D1 or D2 found in the conjugate;

(c) causing D1 to absorb energy; and (d) measuring the level of D2 emission, wherein emission from D2 upon absorption of energy by D1 indicates the presence of the target site in the substance.

14. A conjugate comprising the dye of claim 1 conjugated to a probe, a target, and/or a support.

15. A conjugate comprising the compound of claim 10 conjugated to a probe, an FETL, a target, and/or a support.

16. A proximity assay comprising the steps of:

(a) contacting a substance to be tested and a target-site-specific donor dye in a suitable assay vessle;

(b) introducing a target-site-specific fluorescence energy transfer reporter dye conjugate of claim 14 into the vessel, where said reporter dye's target is either spatially proximate to said donor dye target or specific for a given target to be tested for spatial proximity to said donor dye target, and said reporter dye's energy absorption spectra overlaps the emission spectra of said donor dye;

(c) causing the donor dye to absorb energy; and (d) measuring the level of reporter dye emission, wherein emission from the reporter dye upon absorption of energy by the donor dye indicates the proximity of the donor dye target and the reporter dye target in the substance.

17. The proximity assay of claim 16 wherein:

step (b) further comprises introducing two or more target-site-specific fluorescence energy transfer reporter dye conjugates of claim 14 into the vessel, said reporter dyes having energy absorption spectra overlapping the emission spectra of said donor dye, distinct emission spectra, and having different targets to be tested for spatial proximity to said donor dye target; and step (d) further comprises measuring the level of reporter dye emission at the wavelengths characteristic of said reporter dyes, wherein emission characteristic of each reporter dye upon absorption of energy by the donor dye indicates the respective proximity of the donor dye target to each corresponding reporter dye target in the substance.

* * * * *